United States Patent
Blasius et al.

(10) Patent No.: US 8,389,694 B2
(45) Date of Patent: Mar. 5, 2013

(54) BIOLOGICALLY ACTIVE ANTIBODIES RECOGNIZING A CELL SURFACE MOLECULE SELECTIVELY EXPRESSED ON LIVING MOUSE NATURAL TYPE ONE (I) INTERFERON PRODUCING CELLS

(76) Inventors: Amanda L. Blasius, Boca Raton, FL (US); Marco Colonna, St. Louis, MO (US); Marina Cella, St. Louis, MO (US)

( * ) Notice: Subject to any disclaimer, the term of this patent is extended or adjusted under 35 U.S.C. 154(b) by 1380 days.

(21) Appl. No.: 11/570,118

(22) PCT Filed: Nov. 23, 2004

(86) PCT No.: PCT/US2004/039492
§ 371 (c)(1),
(2), (4) Date: Feb. 19, 2009

(87) PCT Pub. No.: WO2005/052126
PCT Pub. Date: Jun. 9, 2005

(65) Prior Publication Data
US 2009/0214557 A1    Aug. 27, 2009

Related U.S. Application Data

(60) Provisional application No. 60/525,040, filed on Nov. 25, 2003.

(51) Int. Cl.
C12P 21/08    (2006.01)
C07K 16/00    (2006.01)
A61K 39/00    (2006.01)
(52) U.S. Cl. ............... 530/387.7; 530/388.2; 424/184.1
(58) Field of Classification Search .................. None
See application file for complete search history.

(56) References Cited

U.S. PATENT DOCUMENTS

| | | | |
|---|---|---|---|
| 4,865,970 A | 9/1989 | Brot et al. | |
| 5,354,691 A | 10/1994 | Van Eden et al. | |
| 6,232,522 B1 | 5/2001 | Harley et al. | |
| 6,416,973 B1 | 7/2002 | Bakker et al. | |
| 7,572,900 B2 * | 8/2009 | Strasser et al. | 536/23.1 |
| 2008/0305121 A1 | 12/2008 | Ohkawa et al. | |

FOREIGN PATENT DOCUMENTS

WO    2005052126 A3    6/2005

OTHER PUBLICATIONS

Ngo et al. (1994), The Protein Folding Problem and Tertiary Structure Prediction, pp. 491-495.*
Wells et al. (1990), Biochemistry, vol. 29, No. 37, pp. 8509-8517.*
Colonna et al. (2002), Current Opinion in Immunology, vol. 14, pp. 373-379.*
Perussia B, Fanning V, Trinchieri G. A leukocyte subset bearing HLA-DR antigens is responsible for in vitro alpha interferon production in response to viruses. Nat Immun Cell Growth Regul. 1985;4:120-137.
Fitzgerald-Bocarsly P. Human natural interferon-alpha producing cells. Pharmacol Ther. 1993;60:39-62.
Cederblad B, Alm GV. Infrequent but efficient interferon-alpha-producing human mononuclear leukocytes induced by herpes simplex virus in vitro studied by immuno-plaque and limiting dilution assays. J Interferon Res. 1990;10;65-73.
Siegal FP, Kadowaki N, Shodell M, Fitzgerald-Bocarsly PA, Shah K, Ho S, Antonenko S, Liu YJ. The nature of the principal type 1 interferon-producing cells in human blood. Science. 1999;284:1835-1837.
Cella M, Jarrossay D, Facchetti F, Alebardi O, Nakajima H, Lanzavecchia A, Colonna M. Plasmacytoid monocytes migrate to inflamed lymph nodes and produce large amounts of type I interferon. Nat Med. 1999;5:919-923.
Bauer M, Redecke V, Ellwart JW, Scherer B, Kremer JP, Wagner H, Lipford GB. Bacterial CpG-DNA triggers activation and maturation of human CD11c-, CD123+ dendritic cells. J Immunol. 2001;166:5000-5007.
Jarrossay D, Napolitani G, Colonna M, Sallusto F, Lanzavecchia A. Specialization and complementarity in microbial molecule recognition by human myeloid and plasmacytoid dendritic cells. Eur J Immunol. 2001;31:3388-3393.
Kadowaki N, Ho S, Antonenko S, Malefyt RW, Kastelein RA, Bazan F, Liu YJ. Subsets of human dendritic cell precursors express different toll-like receptors and respond to different microbial antigens. J Exp Med. 2001;194:863-869.
Krug A, Towarowski A, Britsch S, Rothenfusser S, Hornung V, Bals R, Giese T, Engelmann H, Endres S, Krieg AM, Hantmann G. Toll-like receptor expression reveals CpG DNA as a unique microbial stimulus for plasmacytoid dendritic cells which synergizes with CD40 ligand to induce high amounts of IL-12. Eur J Immunol. 2001;31:3026-3037.
Krieg AM. CpG motifs in bacterial DNA and their immune effects. Annu Rev Immunol. 2002;20:709-760.
Lund J, Sato A, Akira S, Medzhitov R, Iwasaki A. Toll-like receptor 9-mediated recognition of Herpes simplex virus-2 by plasmacytoid dendritic cells. J Exp Med. 2003;198:513-520.
Cella M, Facchetti F, Lanzavecchia A, Colonna M. Plasmacytoid dendritic cells activated by influenza virus and CD40L drive a potent TH1 polarization, Nat Immunol. 2000,1:305-310.
Asselin-Paturel C, Boonstra A, Dalod M, Durand I, Yessaad N, Dezutter-Dambuyant C, Vicari A, O'Garra A, Biron C, Briera F, Trinchieri G. Mouse type I IFN-producing cells are immature APCs with plasmacytoid morphology. Nat Immunol. 2001;2:1144-1150.
Brasel K, De Smedt T, Smith JL, Maliszewski CR. Generation of murine dendritic cells from flt3-ligand-supplemented bone, marrow cultures. Blood. 2000;96:3029-3039.

(Continued)

Primary Examiner — Christine J Saoud
Assistant Examiner — Jegatheesan Seharaseyon
(74) Attorney, Agent, or Firm — Armstrong Teasdale LLP

(57) ABSTRACT

An isolated and characterized monoclonal antibody ("440c") prepared by immunizing Wistar/CRL rats subcutaneously with purified rat bone marrow IPC, fusing popliteal lymph nodes of the rats with SP2/0 myeloma spleen cells and differentially selecting for hybridome supernatants that successfully stain bone marrow derived IPC and fractions thereof using CD11c+ spleen cells and, differentially selecting for hybridoma supernatants from the CD11c+ spleen cells that successfully stain only CD 11 c+/Ly6c+/CD 11 b–/B220+ splenocytes to provide the monoclonal antibody.

4 Claims, 14 Drawing Sheets

OTHER PUBLICATIONS

Krug A, Uppaluri R, Facchetti F, Dorner BG, Sheehan KC, Schreiber RD, Cella M, Colonna M. IFN-producing cells respond to CXCR3 ligands in the presence of CXCL12 and secrete inflammatory chemokines upon activation. J Immunol. 2002;169:6079-6083.

Penna G, Vulcano M, Sozzani S, Adorini L. Differential migration behavior and chemokine production by myeloid and plasmacytoid dendritic cells. Hum Immunol. 2002;63:1164-1171.

Fonteneau JF, Gilliet M, Larsson M, Dasilva I, Munz C, Liu YJ, Bhardwaj N. Activation of influenza virus-specific CD4+ and CD8+ T cells: a new role for plasmacytoid dendritic cells in adaptive immunity. Blood. 2003;101:3520-3526.

Dalod M, Salazar-Mather TP, Malmgaard L, Lewis C, Asselin-Paturel C, Briere F, Trinchieri G, Biron CA. Interferon alpha/beta and interleukin 12 responses to viral infections: pathways regulating dendritic cell cytokine expression in vivo. J Exp Med. 2002;195:517-528.

Krug A, Veeraswamy R, Pekosz A, Kanagawa O, Unanue ER, Colonna M, Cella M. Interferon-producing cells fail to induce proliferation of naive T cells but can promote expansion and T helper 1 differentiation of antigen-experienced unpolarized T cells. J Exp Med. 2003;197:899-906.

Boonstra A, Asselin-Paturel C, Gilliet M, Crain C, Trinchieri G, Liu YJ, O'Garra A. Flexibility of mouse classical and plasmacytold-derived dendritic cells in directing T helper type 1 and 2 cell development on antigen dose and differential toll-like receptor ligation. J Exp Med. 2003;191:101-109.

Vollenweider R, Lennert K. Plasmacytoid T-cell clusters in non-specific lymphadenitis. Virchows Arch B Cell Pathol Incl Mol Pathol. 1983;44:1-14.

Facchetti F, De Wolf-Peters C, Marocolo D, De Vos R. Plasmacytoid monocytes in granulomatous lymphadenitis and in histiocytic necrotizing lymphadenitis. Sarcoidosis. 1991;8:170-171.

Nakano H, Yanagita M, Gunn MD. CD11c(+)B220(+)Gr-1(+) cells in mouse lymph nodes and spleen display characteristics of plasmacytoid dendritic cells. J Exp Med. 2001;194:1171-1178.

Vanbervliet B, Bendriss-Vermare N, Massacrier C, Homey B, De Bouteiller O, Briere F, Trinchieri G, Caux C. The Inducible CXCR3 Ligands Control Plasmacytoid Dendritic Cell Responsiveness to the Constitutive Chemokine Stromal Cell-derived Factor 1 (SDF-1)/CXCL12. J Exp Med. 2003;198:823-830.

Smith CM, Belz GT, Wilson NS, Villadangos JA, Shortman K, Carbone FR, Heath WR. Cutting edge: conventional CD8 alpha+ dendritic cells are preferentially involved in CTL priming after footpad infection with herpes simplex virus-1. J Immunol. 2003;170:4437-4440.

Bjorck P. Isolation and characterization of plasmacytoid dendritic cells from Flt3 ligand and granulocyte-macrophage colony-stimulating factor-treated mice. Blood. 2001;98:3520-3526.

Dumont FJ, Coker LZ. Interferon-alpha/beta enhances the expression of Ly-6 antigens on T cells in vivo and in vitro. Eur J Immunol. 1986;16:735-740.

Schlueter AJ, Krieg AM, de Vries P, Li X. Type I interferon is the primary regulator of inducible Ly-6C expression on T cells. J Interferon Cytokine Res. 2001;21:621-629.

Heldwein KA, Fenton MJ. The role of Toll-like receptors in immunity against mycobacterial infection. Microbes Infect. 2002;4:937-944.

Brightbill HD, Libraty DH, Krutzik SR, Yang RB, Belisle JT, Bleharski JR, Maitland M, Norgard MV, Plevy SE, Smale ST, Brennan PJ, Bloom BR, Godowski PJ, Modlin RL. Host defense mechanisms triggered by microbial lipoproteins through toll-like receptors. Science. 1999;285:732-736.

Barchet W, Cella M, Odermatt B, Asselin-Paturel C, Colonna M, Kalinke U. Virus-induced interferon alpha production by a dendritic cell subset in the absence of feedback signaling in vivo. J Exp Med. 2002;195:507-516.

Eloranta ML, Alm GV. Splenic marginal metallophilic macrophages and marginal zone macrophages are the major interferon-alpha/beta producers in mice upon intravenous challenge with herpes simplex virus. Scand J Immunol. 1999;49:391-394.

Zou W, Machelon V, Coulomb-L'Hermin A, Borvak J, Nome F, Isaeva T, Wei S, Krzysiek R, Durand-Gasselin I, Gordon A, Pustilnik T, Curiel DT, Galanaud P, Capron F, Emilie D, Curiel TJ. Stromal-derived factor-1 in human tumors recruits and alters the function of plasmacytoid precursor dendritic cells. Nat Med. 2001;7:1339-1346.

Dzionek A, Sohma Y, Nagafune J, Cella M, Colonna M, Facchetti F, Gunther G, Johnston I, Lanzavecchia A, Nagasaka T, Okada T, Vermi W, Winkels G, Yamamoto T, Zysk M, Yamaguchi Y, Schmitz J. BDCA-2, a novel plasmacytoid dendritic cell-specific type II C-type lectin, mediates antigen capture and is a potent inhibitor of interferon alpha/beta induction. J Exp Med. 2001;194:1823-1834.

Ronnblom L, Alm GV. An etiopathogenic role for the type I IFN system in SLE. Trends Immunol. 2001;22:427-431.

Vallin H, Perers A, Alm GV, Ronnblom L. Anti-double-stranded DNA antibodies and immunostimulatory plasmid DNA in combination mimic the endogenous IFN-alpha inducer in systemic lupus erythematosus. J Immunol. 1999;163:6306-6313.

Jego G, Palucka AK, Blanck JP, Chalouni C, Pascual V, Banchereau J. Plasmacytoid dendritic cells induce plasma cell differentiation through type I interferon and interleukin 6. Immunity. 2003;19:225-234.

Farkas L, Beiske K, Lund-Johansen F, Brandtzaeg P, Jahnsen FL. Plasmacytoid dendritic cells (natural interferon-alpha/beta-producing cells) accumulate in cutaneous lupus erythematosus lesions. Am J Pathol. 2001;159:237-243.

Bennett L, Palucka AK, Arce E, Cantrell V, Borvak J, Banchereau J, Pascual V. Interferon and granulopoiesis signatures in systemic lupus erythematosus blood. J Exp Med. 2003;197:711-723.

Natural Alpha Interferon-Producing Cells Respond to Human Immunodeficiency Virus Type 1 with Alpha Interferon Production and Maturation in Dendritic Cells, Akihito Yonezawa, et al., Journal of Virology, 2003 Mah; 77(6): 377-3784.

Flavell DJ. Saporin immunotoxins. Curr Top Microbiol Immunol. 1998;234:57-61.

Blasius et al., "A cell surface molecule selectively expressed on murine Natural Interferon Producing Cells that blocks secretion of interferon-alpha.", Blood First Edition Paper, prepublished online Dec. 24, 2003; DOI 10.1182/blood-2003-9-3108, pp. 1-33.

* cited by examiner

A-D

E-F

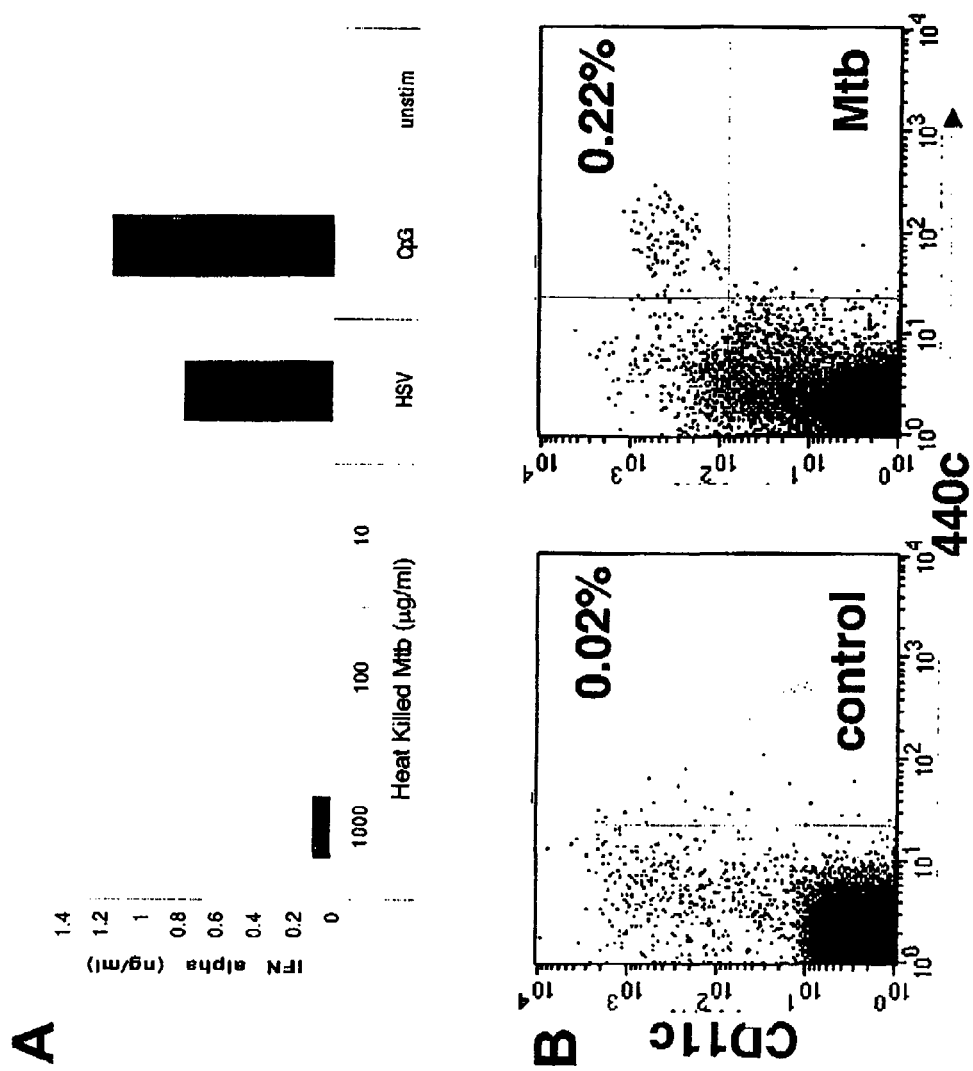
Figure 5 A-B

C-D

BIOLOGICALLY ACTIVE ANTIBODIES RECOGNIZING A CELL SURFACE MOLECULE SELECTIVELY EXPRESSED ON LIVING MOUSE NATURAL TYPE ONE (I) INTERFERON PRODUCING CELLS

CROSS REFERENCE TO RELATED APPLICATIONS

This application claims the priority of U.S. Provisional Patent Application Ser. No. 60/525,040, filed Nov. 25, 2003, and PCT International Patent Application Number PCT/US2004/039492, filed Nov. 23, 2004, both of which are hereby incorporated by reference in their entirety.

This application claims the priority of U.S. Provisional Patent Application 60/525,040 filed Nov. 25, 2003 which is incorporated herein in its entirety by reference.

A portion of the disclosure of this patent document contains material which is subject to copyright protection. The copyright owner has no objection to the facsimile reproduction by anyone of the patent document or the patent disclosure as it appears in the U.S. Patent and Trademark Office patent file or records, but otherwise reserves all copyright rights whatsoever.

FIELD OF THE INVENTION

This discovery relates generally to functional novel biologically active antibodies which selectively recognize an IPC cell surface molecule that regulates secretion of Type I interferons in living mice. In particular this discovery relates to a 440c mAb. This invention has diagnostic and therapeutic utilities.

More particularly this invention relates to use of an antibody having the specificity of a 440c antibody to diagnose the role of IPC in a biosystem of healthy and diseased murine (diagnosis) and to treat diseases like lupus, sarcoidosis and arthritis like symptomatology (therapeutic). Further, this invention relates to a living murine animal model system involving IPC secreting Type I interferons, and useful methods of use of that murine animal model system for screening pharmaceutical chemicals efficacious against Type I interferons secreting cells in murine animal models and to determine the role of IPC if any, in a disease state murine.

BACKGROUND OF THE INVENTION

Scientists have long desired to more particularly understand the nature of inflammation of an immune response particularly in a diseased state clinically triggered by a virus or microbe. An understanding of virally or microbially infected cell behavior leading to a clinical diagnosis and treatment regime is highly desired to treat living diseased animals having chronic destructive autoimmune or autoimmune like diseases. Such understanding is intrinsically linked to a desire by medical practitioners to alleviate at least one of (a) a symptom of an infection, (b) excessive immune response (s) due to autoimmunity and (c) ineffective immune response caused by immunodeficiency. Practitioners desire to provide curative treatment to an underlying disease state of a distressed living human so that patient suffering is at least somewhat alleviated.

Type 1 interferons, proteins generated by natural interferon producing cells, are of particular significance in scientific studies and medicinal research. The level (i.e. concentration in mg/ml) of Type I interferons typically measured in serum recovered from blood is modulated in diseased state animals or in tissues of diseased state animals as compared to levels in healthy animals.

Natural interferon producing cells (IPC) were originally identified in human blood as a small subset of leukocytes that secrete high levels of interferon (IFN)-α and β when incubated in vitro with a variety of DNA and RNA viruses, including herpes simplex virus type 1 (HSV-1), cytomegalovirus (CMV), Sendai virus and influenza virus[1-5]. More recently, it was shown that human and murine IPC also respond to single stranded oligodeoxynucleotides (ODN) containing deoxycytidylate-phosphate-deoxyguanylate (CpG) Motifs[6-9], which mimic unmethylated CG dinucleotides found in microbial DNA[10]. Recognition of CpG ODN and certain viruses by IPC is mediated by Toll-like receptor 9 (TLR9)[11]. In addition to IFN-α and -β, IPC secrete IL-12[12-14] and proinflammatory chemokines in response to viruses and CpG ODN[15-17]. Together, these cytokines and chemokines modulate the antigen presenting function of dendritic cells (DC)[18], as well as recruiting and activating NK cells and T cells[18]. Furthermore, IPC themselves function as antigen presenting cells that expand memory T cells and induce Th1 differentiation[17-20].

To interact with and activate NK cells, it is hypothesized that T cells and antigen presenting cells, IPC must migrate from the blood into lymph nodes during an immune response in vivo. Consistent with this hypothesis, human IPC are particularly abundant in inflamed lymph nodes of human individuals affected by chronic infections or autoimmune diseases, especially around high endothelial venules (HEVs)[21, 22]. Moreover, IPC express homing molecules and chemokine receptors that can direct IPC migration from the blood into inflamed lymph nodes through HEVs[5,15,23,24].

Although human IPC have been known for almost two decades, mouse IPC have been identified only recently. Furthermore, it has now been shown that IPC correspond with the enigmatic 'plasmacytoid cells' or 'plasmacytoid' identified in human lymph nodes during infections. These notions have brought IPC to the attention of immunologists for their role in innate immunity and in shaping T cell and B cell responses.

Demonstrating IPC recruitment and function in murine infection models has been difficult up to this time because multiple antibodies are required to distinguish IPC from other immune cells and very few can be recovered from lymphoid organs such as lymph nodes.

In mice, footpad immunization with HSV-1 induces a modest influx of IPC in draining lymph nodes[25]. To date, however, there is no experimental evidence that IPC accumulate in lymph nodes as a direct result of inflammation. Demonstrating IPC accumulation in mouse lymph nodes is difficult due to the low numbers of IPC and their complex phenotype (CD11c$^+$, Ly-6C$^+$, Gr-1$^+$, B220$^+$, CD11b$^-$, CD8a$^{+/-}$)[13,23,26]. A method of detecting IPC is highly desired.

Systemic lupus erythematosus (SLE) and SLE similar type diseases are of particular interest in the diagnosis and treatment of chronic devastating autoimmune diseases. Human patients with SLE would be expected to have an activated type I interferon system with ongoing Type I interferon synthesis (secretion).

Lupus is a particularly insidious destructive human autoimmune disease wherein the host's immune system attacks and destroys the human host's own body. Clinical features of lupus include inflammation, pain, fatigue and other possible long lasting host organ damage. It is highly desired to have an effective clinical medical treatment for this very painful debilitating and potentially fatal multisystem disease.

NIH Publication 02-5060 describes sarcoidosis as a disease that causes inflammation of the body's tissues. According to this NIH publication, inflammation of sarcoidosis can occur in almost any organ and always affects more than one organ.

Another devastating immune disease, arthritis, comprises more than one hundred different conditions. These conditions range from mild forms of tendinitis and bursitis to crippling systemic forms, such as rheumatoid arthritis. There are pain syndromes such as fibromyalgia, polymyalgia-rheumatica and other arthritis-related disorders, such as systemic lupus erythematosus "(SLE)", that literally involve every part of the body. There are other forms of immune disease, such as gout and osteoarthrosis (or osteoarthrosis).

Despite notable advances in understanding of Type I interferon secreting cells in living animals, it is still highly desired to identify and prepare antibody recognizing mice Type I interferon secreting cells and to have an effective murine living animal model(s) for determining the role played by IPC in an autoimmune inflammation state and for evaluating the efficiency of treatment of autoimmune disease state in murines with potentially therapeutic drug candidate(s).

While many scientific investigators have intensively investigated cellular and molecular mechanisms involved in the inflammation process and biometric aspects of such systems, particularly those involving SLE, therapeutic assessment, diagnostic and treatment regimes are still highly desired to be clearly determined as autoimmune diseased patients continue to suffer from painful afflictions.

Murine models of diseases, including viral, bacterial, cancerous and autoimmune, often mimic human diseases. Learning the role of IPC or type I interferons in these murine models will lend insight into the human disease counterpart.

BRIEF DESCRIPTION OF THE INVENTION

In a first embodiment, the discovery comprises isolated, purified, recovered and characterized functional monoclonal antibodies which binds to a common antigen that is the DAP12 adaptor chain associated molecule that is specifically expressed by only IPC and not other cell types. In an aspect the antibody is a 440c antibody. In another aspect these antibodies have the same or substantially the same specificity to that antigen as mAb 440c. DAP12 is a molecule previously identified by another group. DAP 12's Genbank accession number is #AF024637.

In an aspect, this family of antibodies and specifically 440c antibody are successfully prepared, i.e.: obtained, and recovered by intentionally immunizing healthy Wistar/CRL rats subcutaneously with purified mouse bone marrow IPC, fusing popliteal lymph nodes of the rats with immortal SP2/0 myeloma, selecting hybridoma supernatants that successfully stain bone marrow derived IPC and that also stained fractions of CD11C+ spleen cells, differentiatively selecting for hybridoma supernatants that successfully stained CD11C+/Ly-6+/CD11b– splenocytes and recovering such supernatants containing the 440c monoclonal antibody to provide 440c as the desired recovered 440c monoclonal antibody. A binding test (determination) is carried out to determine if an antibody excluding binds to CD11c+Ly6c+B220+CD11b– splenocytes. If an antibody successfully binds to CD11c+Ly6c+B220+CD11b– splenocytes and not other cell types and does not stain any cells in DAP12 deficient mice, then the antibody is determined to be the desired derived antibody.

In an aspect, the novel isolated, purified and characterized monoclonal functional antibodies of this discovery include a fragment and fragments thereof which specifically recognize mouse IPC cell surface molecule that regulates secretion of Type I interferons therefrom.

In an aspect, an antibody composition comprises such antibodies which recognize a mouse IPC cell surface molecule that regulates secretion of Type I interferons and optionally a pharmaceutically acceptable carrier.

In an aspect, a method of refining IPC from a multicomponent proteinaceous aqueous composition comprising 440c mAb antibody conjugateable IPC and other cell types comprises effectively contacting the multicomponent proteinaceous aqueous composition with an effective amount of 440c mAb in the form of at least one of a magnetically attracted metallic particle antibody complex and an antiantibody metallic magnetically attracted particle complex under sufficient time and reaction conditions to allow the at least one antibody complex to bind to the IPC forming an antibody bound IPC subjecting the antibody bound IPC to a magnetic field whereby the antibody bound IPC is magnetic direction maintained; removing the effect of the magnetic field on the antibody IPC; and recovering IPC as purified IPC by separating IPC from the IPC bound composition in a cell culture medium. In an aspect the cell culture medium comprises PBS with 10% serum and a 0.5-2 mM EDTA composition. Alternatively, cell culture medium can be comprised of RPMI1640 or DMEM. In an aspect the refining comprises concentrating the IPC and then isolating IPC from the other cell types.

In an aspect, a method of transferring IPC from a murine to another different murine comprises transferring concentrated IPC, prepared by a process comprising effectively contacting a multicomponent proteinaceous aqueous composition comprising 440c mAb conjugateable IPC and other cell types composition with an effective amount of 440c mAb in the form of at least one of a magnetically attracted metallic particle antibody complex and an antiantibody metallic magnetically attracted particle complex under sufficient time and reaction conditions to allow the at least one antibody complex to bind to the IPC forming an antibody bound IPC; subjecting the antibody bound IPC to a magnetic field whereby the antibody bound IPC is magnetic direction maintained; removing the effect of the magnetic field of the antibody IPC; and recovering IPC as purified IPC by separating (isolating) IPC from the IPC bound composition in a cell culture medium. In an aspect, the magnetic field is the field of a permanent magnet. In an aspect the cell culture medium comprises PBS with 10% serum and a 0.5-2 mM EDTA composition. Alternatively, in an aspect, cell culture medium can be comprised of RPMI1640 or DMEM. In an aspect the refining comprises concentrating the IPC and then isolating IPC from the other cell types. The concentrated IPC can be transferred into another murine by injection subcutaneously, intravenously or directly into the site of diseased tissue.

In an aspect, mAb 440c is conjugated to a conjugatable fluorochrome that emits detectable light of a certain wavelength when excited. IPC is isolated and concentrated from a heterogenous mixture of cells by incubating the fluorochrome conjugated mAb 440c with the mixture. mAb 440c labeled cells can be detected and sorted into cell culture media (PBS, RPMI or DMEM) by flow cytometry. Alternatively, a fluorochrome conjugated secondary reagent is used to detect unconjugated 440c. One such machine useful for performing cell sorting includes a MoFlo cell sorter (Cytomation contact Dako Cytomation Denmark AIS, Produktions vej 42, DK-2600 Glostrup Denmark).

In an aspect, a method of making a quantitative assessment of the role played by IPC in a SLE type disease state in a living murine comprises 1) Measuring the amount of Type I interferons in serum taken of a non-treated murine diseased by infection of a virus or microbe, 2) Treating the murine with an medicinally effective amount of 440c mAb by administering a pharmacologically effective amount of 440c mAb to the murine, 3) Measuring the amount of Type I interferons in serum taken of the treated murine after passage of a medicinally therapeutic effective time, 4) Comparing the amount of Type I interferons measured in the serum taken of the treated murine with the amount of Type I interferons measured in the serum taken of the murine prior to treatment with 440c mAb. If the amount of Type I interferons measured in serum after treatment is less than the amount of Type I interferons measured in serum before treatment and/or a symptom of the disease or indicator of severity of the disease was affected, then it is determined that IPC played a role.

In an aspect, a method of determining or defining the pathology of an inflammatory disease state in a living murine due to an infection by at least one of a microbial or viral pathogen comprises 1) Measuring the amount of Type I interferons in serum taken of a non-treated murine diseased by infection of a virus or microbe, 2) Treating the murine with an medicinally effective amount of 440c mAb by administering a pharmacologically effective amount of 440c mAb to the murine, 3) Measuring the amount of Type I interferons in serum taken of the treated murine after passage of a medicinally therapeutic effective time, 4) Comparing the amount of Type I interferons measured in the serum taken of the treated murine with the amount of Type I interferons measured in the serum taken of the murine prior to treatment with 440c mAb. If the amount of Type I interferons measured in serum after treatment is less than the amount of Type I interferons measured in serum before treatment and/or a symptom of the disease or indicator of severity of the disease was affected, then it is determined that IPC played a role.

In an aspect, a murine animal model for modeling inflammatory disease states of a murine and a human comprises a cellular system mimicking a diseased living murine afflicted with a disease triggering production (secretion) of Type I interferons and a 440c mAb composition pharmacologically suitable for treatment of the bio-system of the diseased murine. In an aspect, a murine is a mouse.

In an aspect, a method for treating at least one symptom of an inflammatory response, such as a symptom from an inflammatory characterized disease, in a diseased living murine comprises administering an effective pharmacological amount of 440c mAb to a murine patient having need of such treatment to alleviate the at least one inflammatory symptom. In an aspect, the symptom is a symptom associated with lupus in humans.

In an aspect this invention comprises a murine inflammation reaction inhibiting composition comprising an antibody having the specificity of 440c mAb and a pharmaceutically acceptable carrier. In an aspect, the antibody is 440c mAb and a murine is a mouse.

In an aspect, a method of treating lupus like symptomatology in a lupus symptomatology like diseased murine comprises effectively administering a pharmacologically effective amount of an antibody having the specificity of 440c mAb to the murine such that the amount of Type I interferons (in the serum of the murine) is effectively reduced. In an aspect, the antibody is 440 mAb and a murine is a mouse.

In an aspect, a medicinal method for obtaining a immunohistology analysis of a murine afflicted with an inflammatory disease state comprises sampling tissue of an inflammatory system diseased murine and staining the tissue with 440c mAb. Stained tissues can be analyzed by microscopy. In an aspect, a murine is a mouse.

In an aspect, a method for down-regulating the biological activity of IPC secreting Type I interferons in a sample of serum of a diseased state murine characterized by excessive inflammation comprises successfully administering an effective down regulating amount of 440c mAb to the murine, thereby down-regulating the biological activity and rendering the treatment/amelioration of such disease. In an aspect, a murine is a mouse.

In an aspect, a method of treating an autoimmune condition, e.g., a condition involving excessive clinical inflammation of lymphatic glands, by administering to a patient having such autoimmune condition and in need of treatment thereof comprises administering a medicinally effective amount of a therapeutic agent comprising 440c mAb that modulates expression of Type I interferons to an animal.

In an aspect, a method of reducing lupus like symptoms and a clinical method of remediating lupus symptoms in an afflicted diseased murine comprises treating that afflicted murine with an effective medicinal amount of 440c mAb. In an aspect, a murine is a mouse.

In an aspect, a method of successfully delivering drugs specifically to IPC comprises effectively conjugating the drug to 440c and effectively administering the conjugate to a murine. In effect, the conjugate will bind specifically to IPC, which will internalize 440c with the conjugated drug. Therefore, the drug can only enter and take effect in IPC. In an aspect, conjugated drugs may include toxins, which may kill IPC, block their function or slow their growth. Alternatively, conjugated drugs may include substances to enhance IPC function, or induce proliferation or survival. In an aspect the murine is a mouse.

BRIEF DESCRIPTION OF THE DRAWINGS

(FIGS. 5C and 5D)

DETAILED DESCRIPTION OF THE DRAWINGS

Figure 1A:
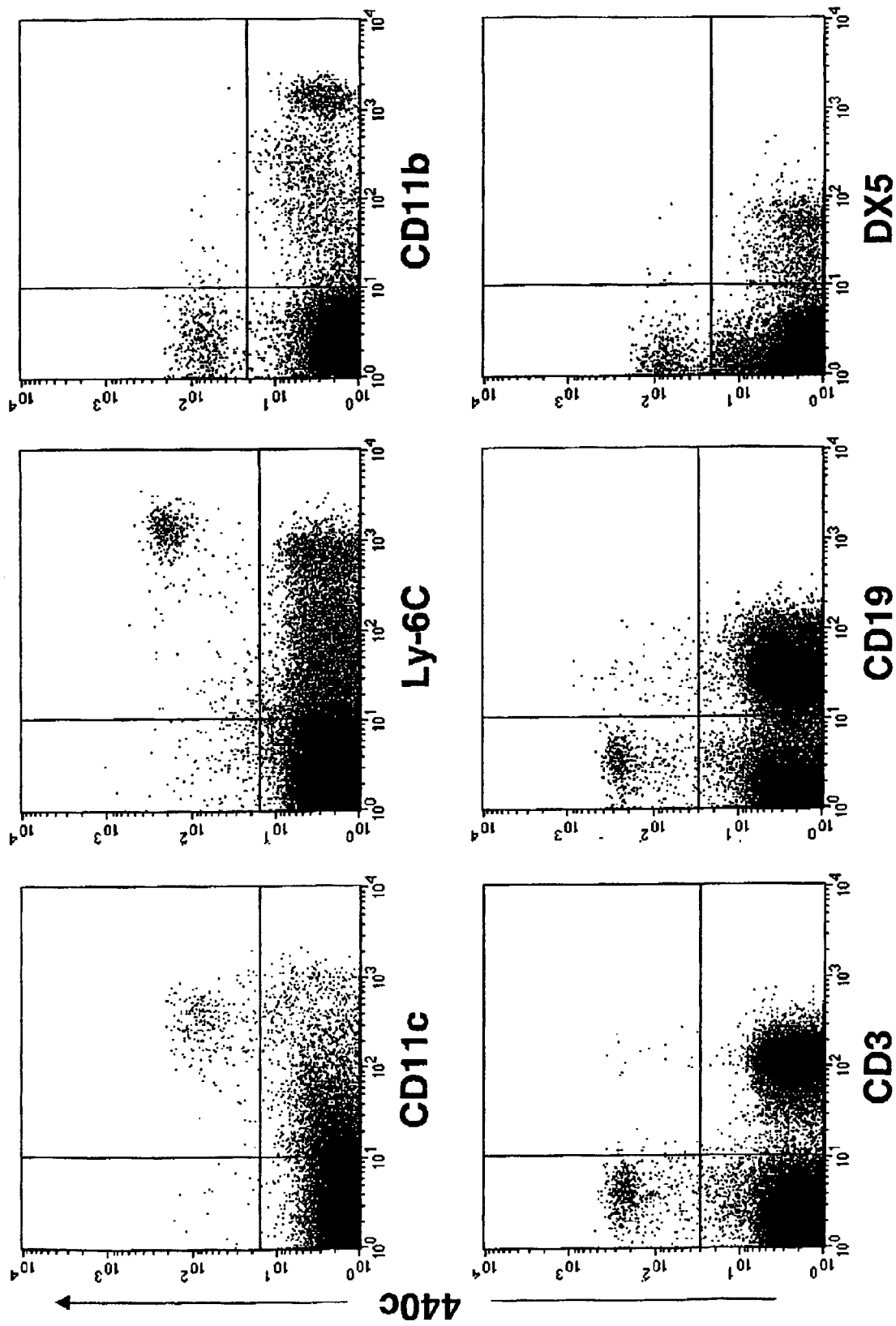
FIG. 1 shows a cellular distribution of 440c antigen within murine splenocytes.
Figure 1B:
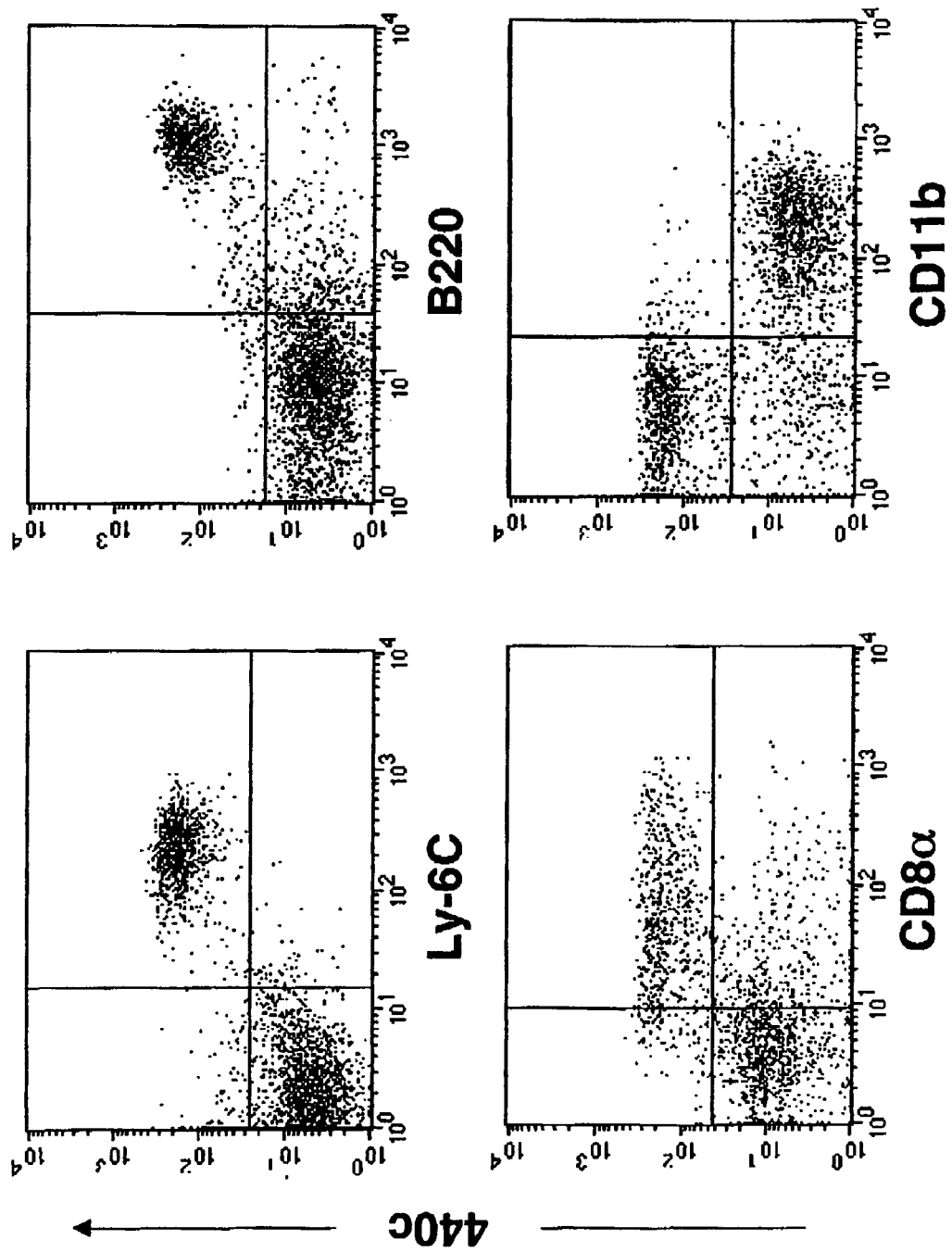
Figure 1C:
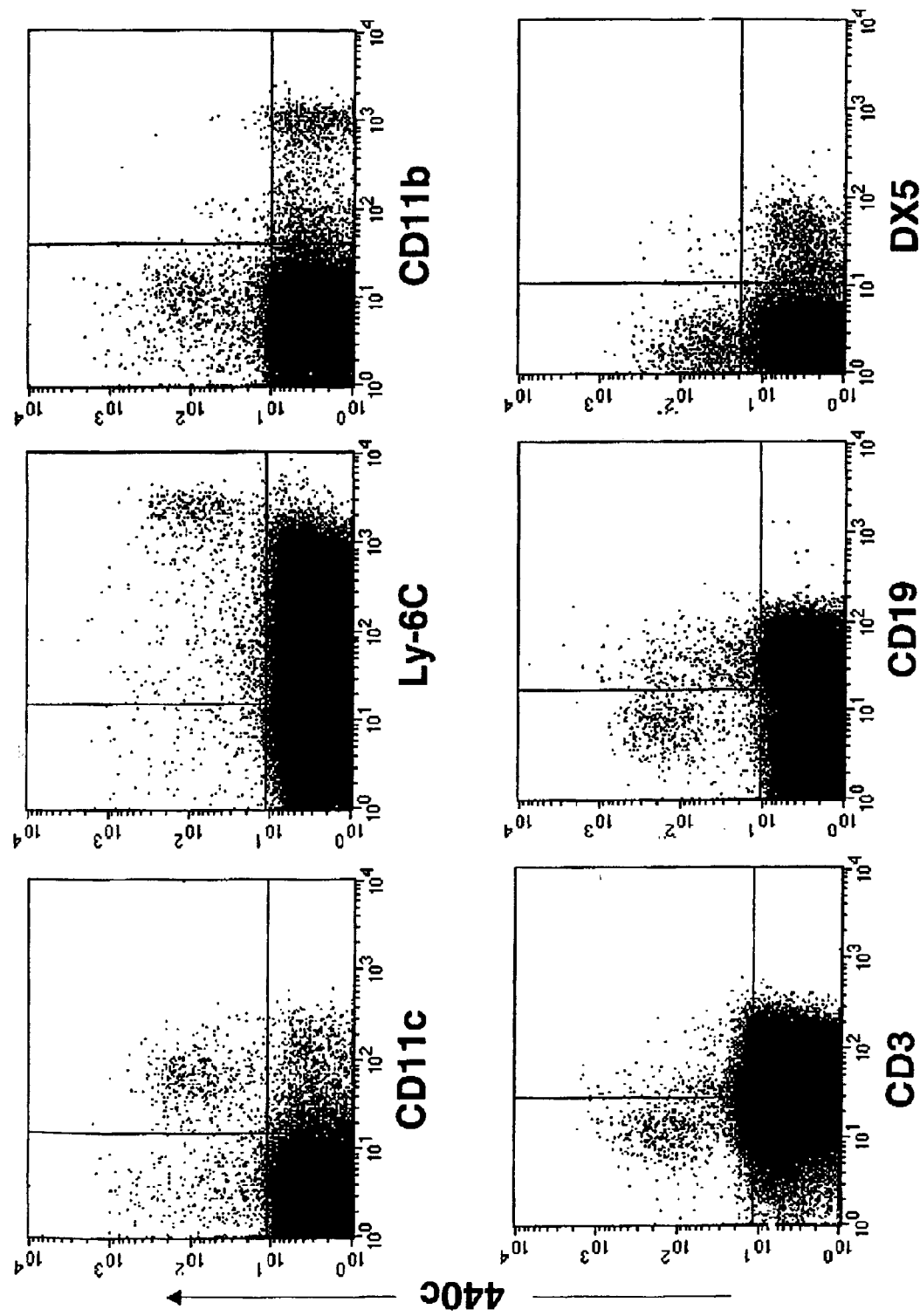

FIG. 1 shows cellular distribution of the inventors' 440c antigen within murine splenocytes. FIG. 1(A) In total splenocytes, our mAb 440c recognizes subsets of CD11c$^+$ and Ly-6C$^+$ cells, but not CD11b$^+$, CD3$^+$, CD19$^+$ or DX5$^+$ cells. FIG. 1(B) Within CD11c-enriched splenocytes, our mAb 440c recognizes a Ly-6C$^+$/B220$^+$/CD8α$^{hi/lo}$/CD11b$^-$ subpopulation. Plots represent gated CD11c+ cells. FIG. 1(C)

mAb 440c recognizes only CD11c+/Ly-6C+ cells within splenocytes derived from mice that have been injected intraperitoneally (i. p.) with MCMV.

Figure 2:
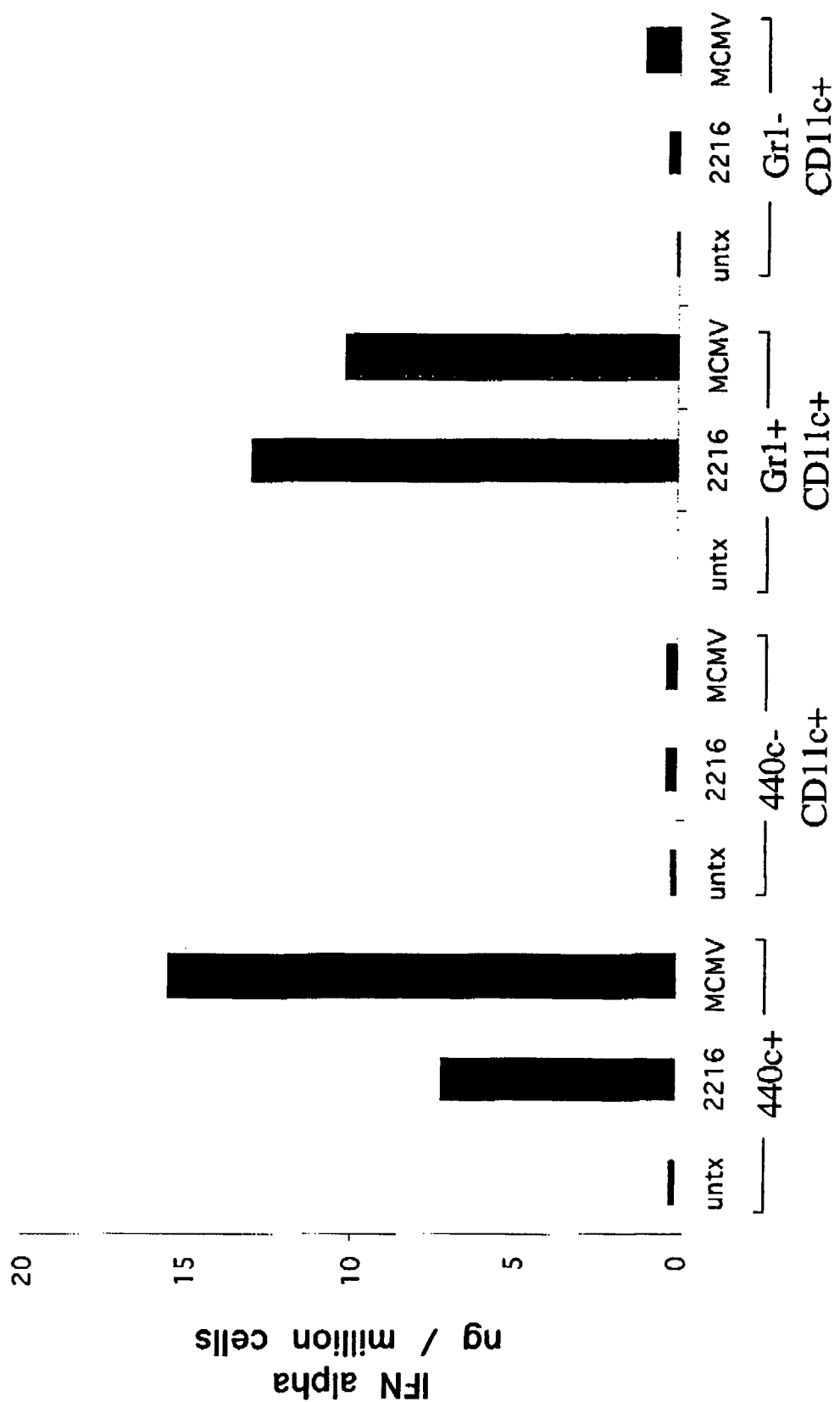
FIG. 2 shows a comparison of IFN-α responses of 440c$^+$, 440c$^-$, CD11c$^+$/Gr-1$^+$/CD11b$^-$ and CD11c$^+$/Gr-1$^-$/CD11b$^{+/-}$ splenocytes to in vitro stimulation with CpG and MCMV. 440c$^+$, 440c$^-$, Gr-1$^+$CD11b$^-$ and Gr-1$^-$/CD11b$^{+/-}$ were sorted from CD11c$^+$ enriched splenocytes and stimulated in vitro with MCMV or CpG ODN 2216 for 24 hours.

FIG. 2 provides a comparison of Type I interferons (IFN-α) responses of 440c+, 440c−, CD11c+/Gr-1+/CD11b− and CD11c+/Gr-1−/CD11b+/− splenocytes to in vitro stimulation with CpG and MCMV. 440c+, 440c−, Gr-1+/CD11b− and Gr-1−/CD11b+/− were sorted from CD11c+ enriched splenocytes and stimulated in vitro with MCMV or CpG ODN 2216 for 24 hours. IFN-α was measured in culture supernatants by ELISA.

Figure 3:
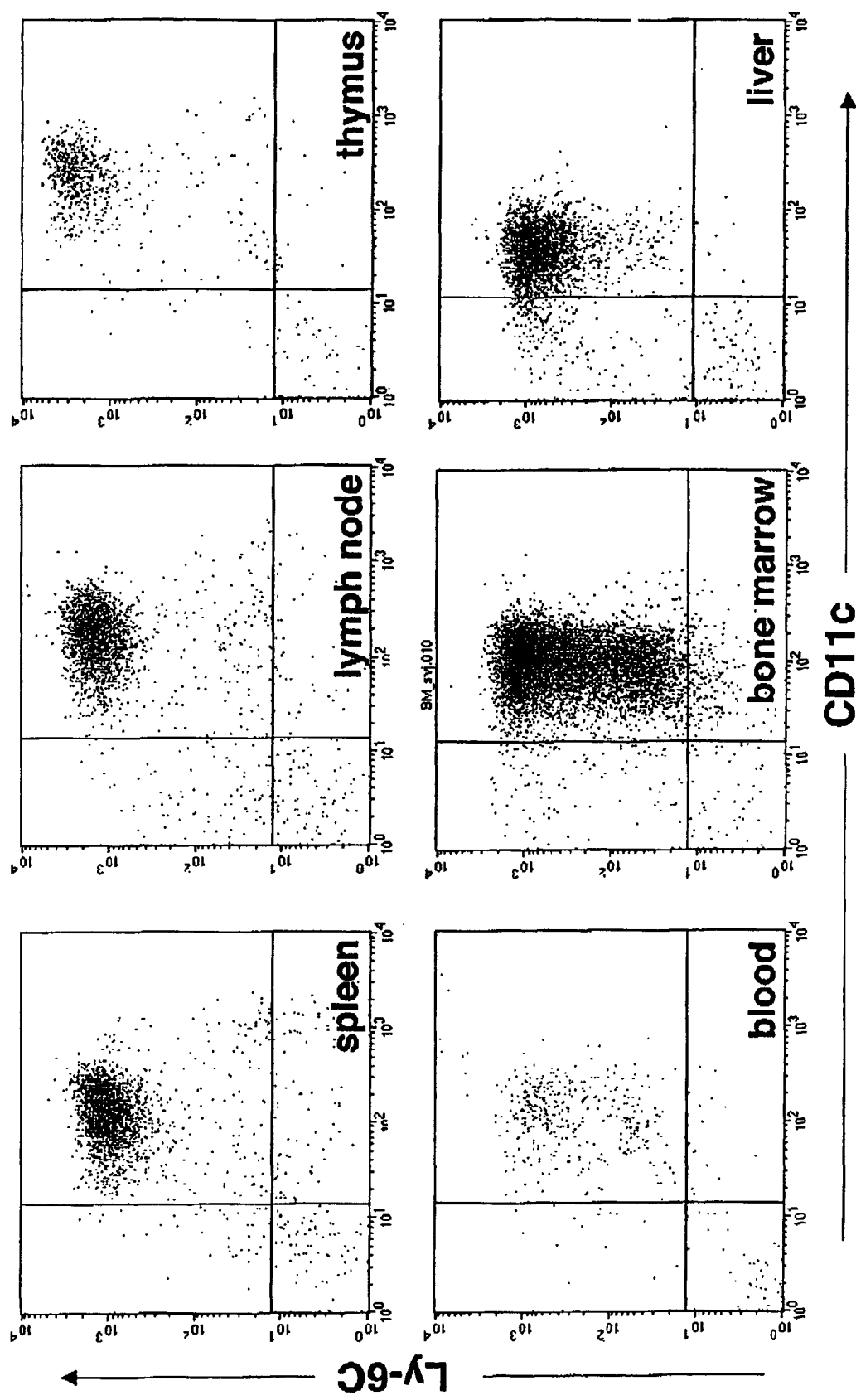
FIG. 3 shows 440c mAb successfully identifying IPC in immune organs and liver.

FIG. 3 shows mAb 440c successfully and specifically identifying IPC in all immune organs and liver. Total cell populations from 129SvJ spleen, peripheral lymph nodes, thymus, bone marrow, liver and blood were stained with 440c, ly-6C, and CD11c. Plots represent gated 440+ cells. Equal numbers of events were collected from spleen, thymus, lymph nodes, bone marrow and liver.

Figure 4:
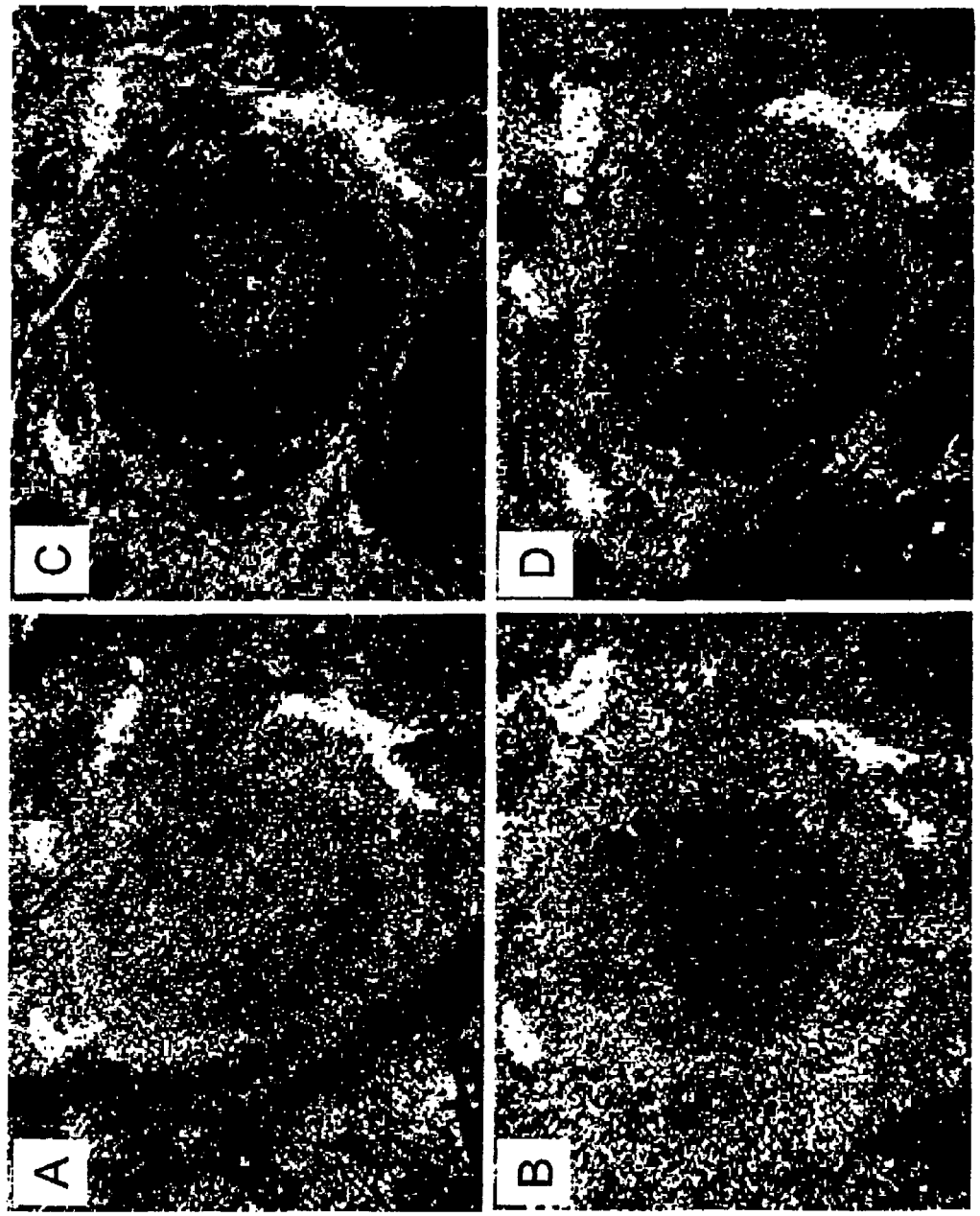
FIG. 4 shows the location of IPC within normal spleen and thymus.
Figure 4:
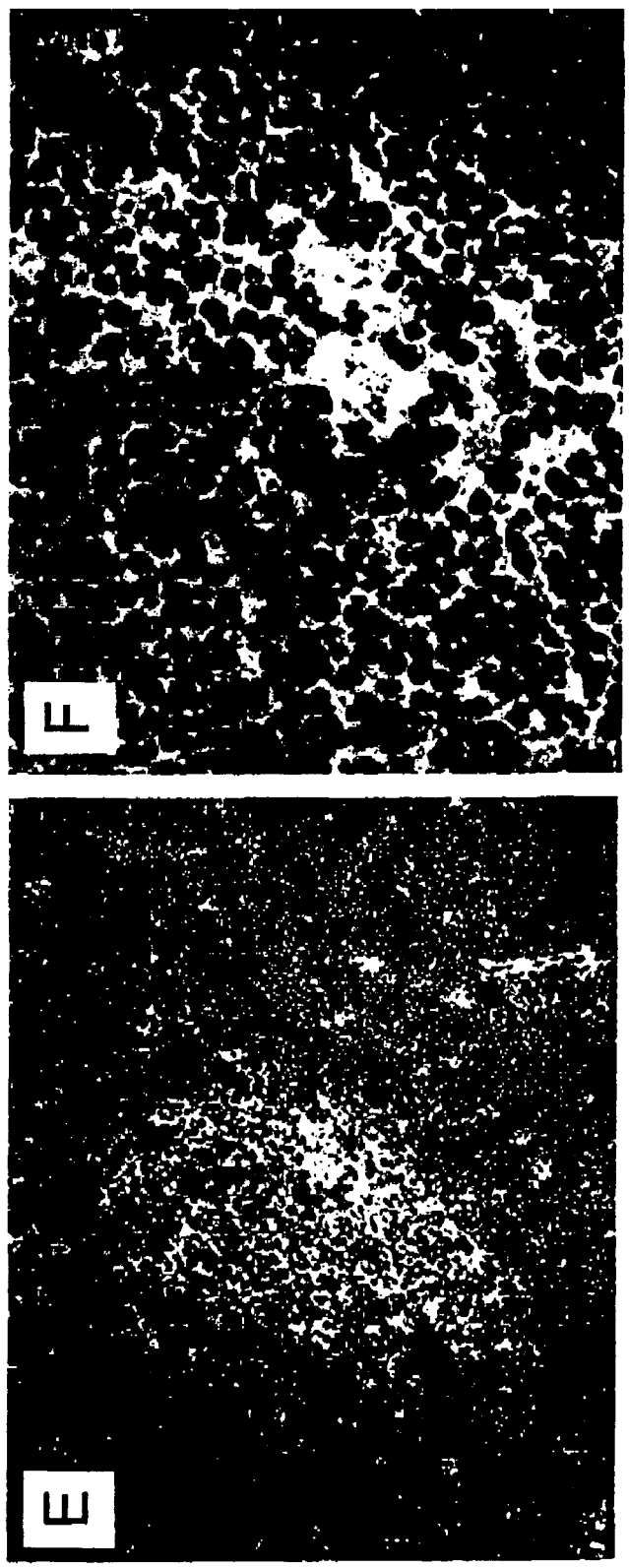

FIG. 4 shows the location of IPC within normal spleen and thymus. FIG. 4(A) shows that abundant 440c+IPC are evident in the periarteriolar sheet (PALS) and at the border of PALS with mantle zone B cells. Serial histological sections were stained with anti-CD3 FIG. 4(B), anti-B220 FIG. 4(C) and anti-IgD FIG. 4(D) to identify the T cell and the B cell zones in the white pulp. Rare IPC are also visible in the red pulp. FIG. 4(E-F) 440c+ IPC are evident in the medulla of the thymus.

Figure 5:
FIGS. 5A, 5B, 5C and 5D show data of an accumulation of IPC in inflamed lymph nodes. Infiltrating IPC were mostly present in the T cell zone.
Figure 5:

FIG. 5 shows an accumulation of IPC in inflamed lymph nodes. FIG. 5(A) Heat killed Mtb does not trigger secretion of IFN-α by IPC in vitro. Bone marrow derived IPC were incubated with varying concentration of heat killed Mtb and IFN-α response was measured by ELISA. Controls include stimulation with HSV-1 (1 MOI), CpG ODN 2216 (3 µg/ml) and no stimulation. FIG. 5(B) 440c+/CD11c+ IPC in lymph nodes draining either the site of inflammation (right plot) or the contralateral site (left plot). The % of IPC is indicated. Equal numbers of events are shown in each plot. FIG. 5(C-D) IPC in histologic sections of lymph nodes draining either the site of inflammation FIG. 5(C) or the contralateral site FIG. 5(D). 129/SvJ mice were inoculated with heat killed Mtb in the left hind leg and footpad twice at a 48 hrs interval. At 72 hours, inguinal and popliteal lymph nodes were separately harvested from the left and right sides of the mouse. Total cell populations were stained with 440c and CD11c. Lymph node sections were analyzed by immunohistochemistry.

Figure 6:
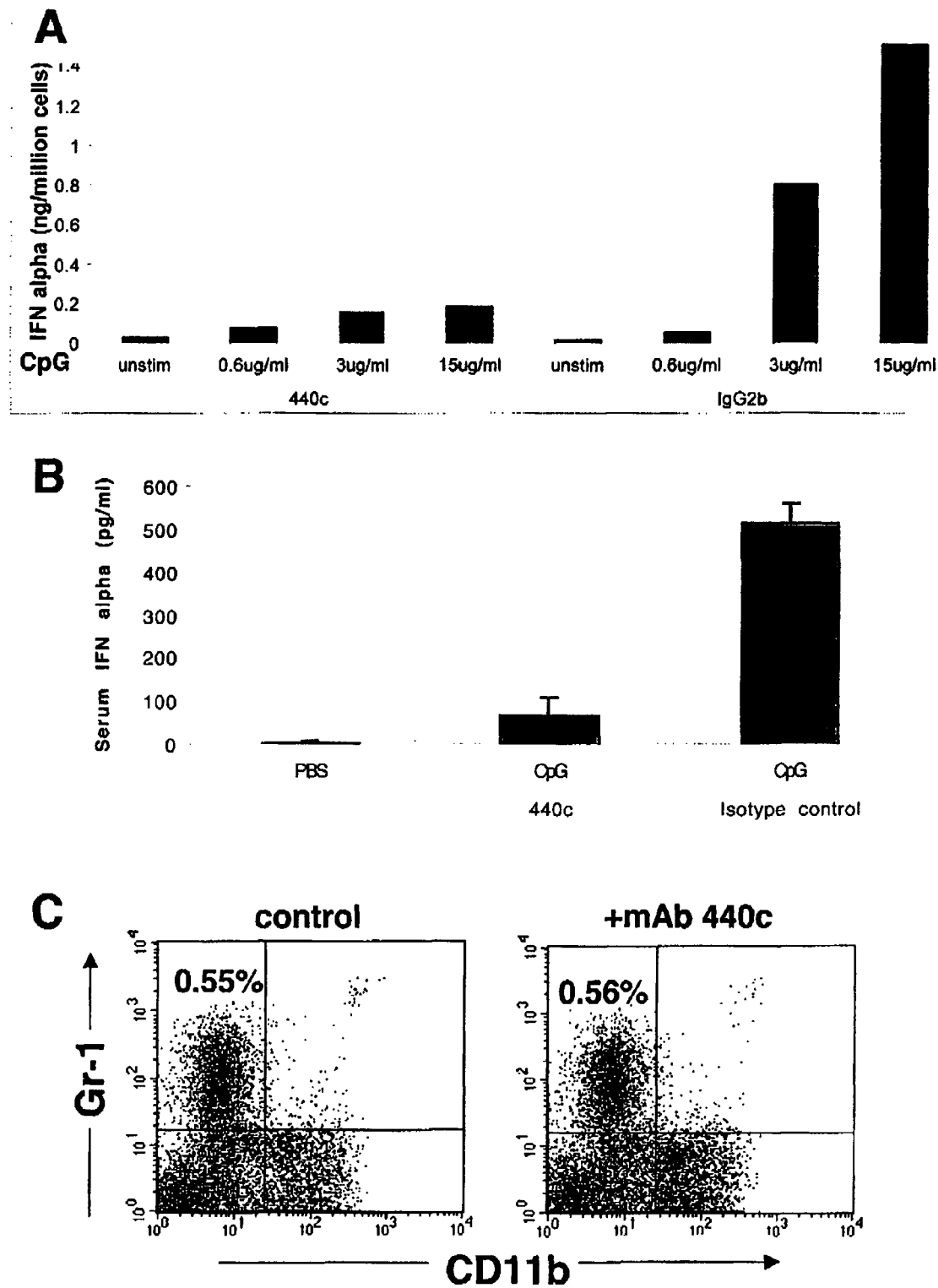
FIG. 6 shows IFN-α response of IPC to CpG after in vitro or in vivo treatment with mAb 440c.

FIG. 6 shows IFN-α response of IPC to CpG after in vitro or in vivo treatment with our mAb 440c. FIG. 6(A) In vitro cross-linking of IPC with mAb 440c blocks IFN-α secretion. IPC were sorted from the spleen and cultured with CpG 2216 ODN on plates coated with mAb 440c or control rat IgG2b. After 24 hrs, IFN-α was measured in culture supernatants by ELISA. Representative data of one out of three separate experiments are shown. FIG. 6(B) In vivo treatment of mice with mAb 440c reduces serum levels of IFN-α. 129/SvJ mice were simultaneously treated s. c. with CpG 2216 ODN or PBS and i. p. with mAb 440c or control rat IgG2b. After 16 hours serum levels of IFN-α were detected by ELISA. Results are expressed as the mean of three mice per group with standard deviation indicated. Representative data of one out of three independent experiment are shown. FIG. 6(C) In vivo treatment with mAb 440c does not deplete IPC. 129/SvJ mice were treated with two i. p. injections each of 200 µg of mAb 440c at a 24 hrs interval. Splenocytes were isolated 24 hrs after the last injection and subjected to flow cytometric analysis. These figures show expression of Gr-1 and CD11b on gated CD11c+ cells. The % of CD11c+/Gr-1+/CD11b− IPC is indicated. Results are representative of three separate tests.

Figure 7:
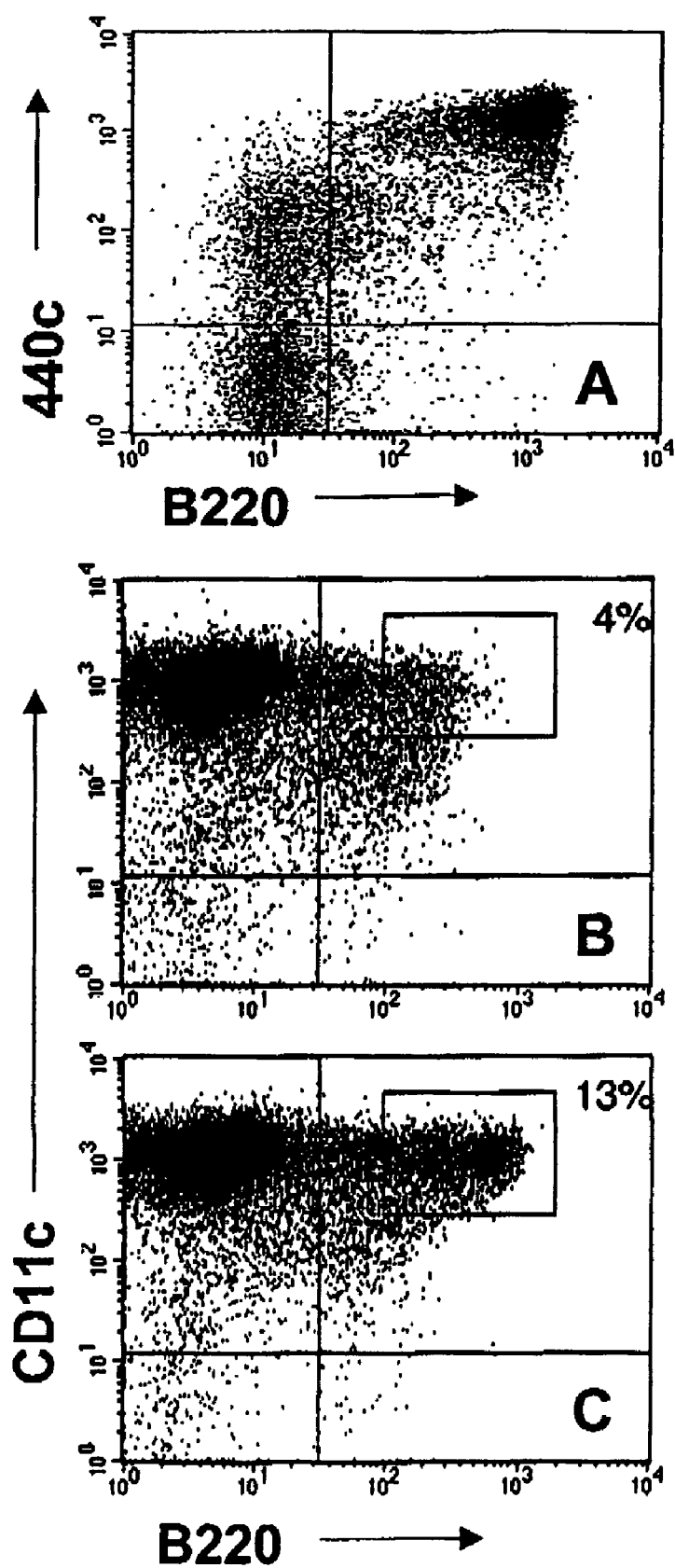
FIG. 7 shows that 440c conjugated with the toxin saporin specifically kills IPC.

FIG. 7 shows sequential treatment with our mAb 440c and saporin depletes IPC in vitro. FIG. 7(A) Expression of 440c on bone marrow cells cultured in FLT3-L for 10 days. CD11c− cells were excluded from the gate. 440c is highly expressed on B220+ cells, which represent fully developed IPCs. FIG. 7(B-C) Depletion of CD11c+/B220+ cells from FLT3-L-derived bone marrow IPC by treatment with 440c-saporin. Cells were stained on ice with biotinylated-440c FIG. 7(B) or a biotinylated control antibody FIG. 7(C), followed by avidin-saporin, cultured for additional 36 hrs and analyzed for residual presence of CD11c+/B220+ cells. The percentage of gated cells is indicated. Our results are representative of three separate experiments.

Figure 8:
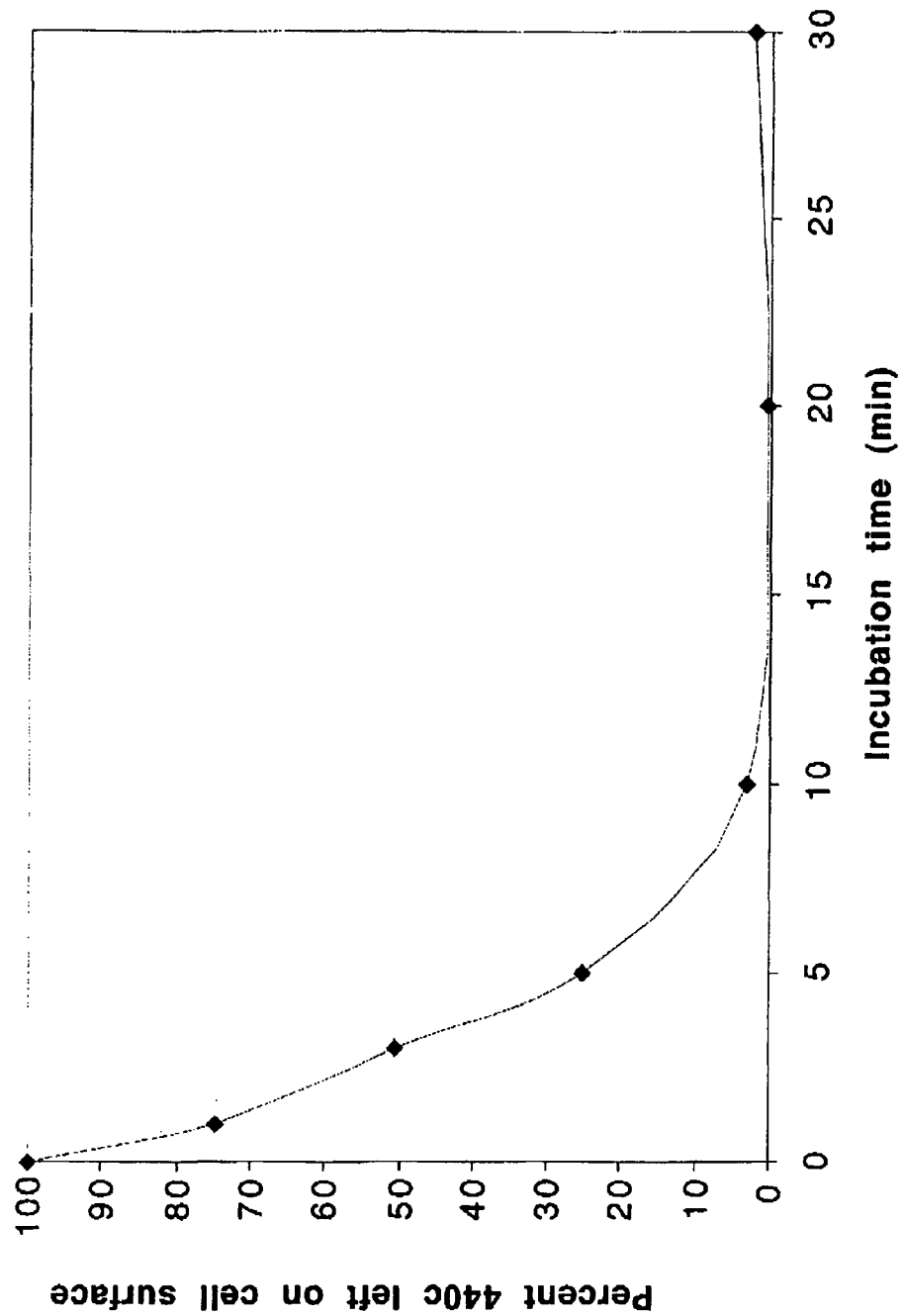
FIG. 8 shows that 440c is rapidly internalized upon binding to IPC.

FIG. 8 shows internalization of 440c on IPC. In vitro bone marrow derived IPC were stained with 440c on ice, washed, and incubated in media at 37° for the indicated times. The level of 440c remaining on the cell surface was determined by FACS. Shown is the mean level of 440c remaining on the cell surface after various incubation times.

Figure 9:
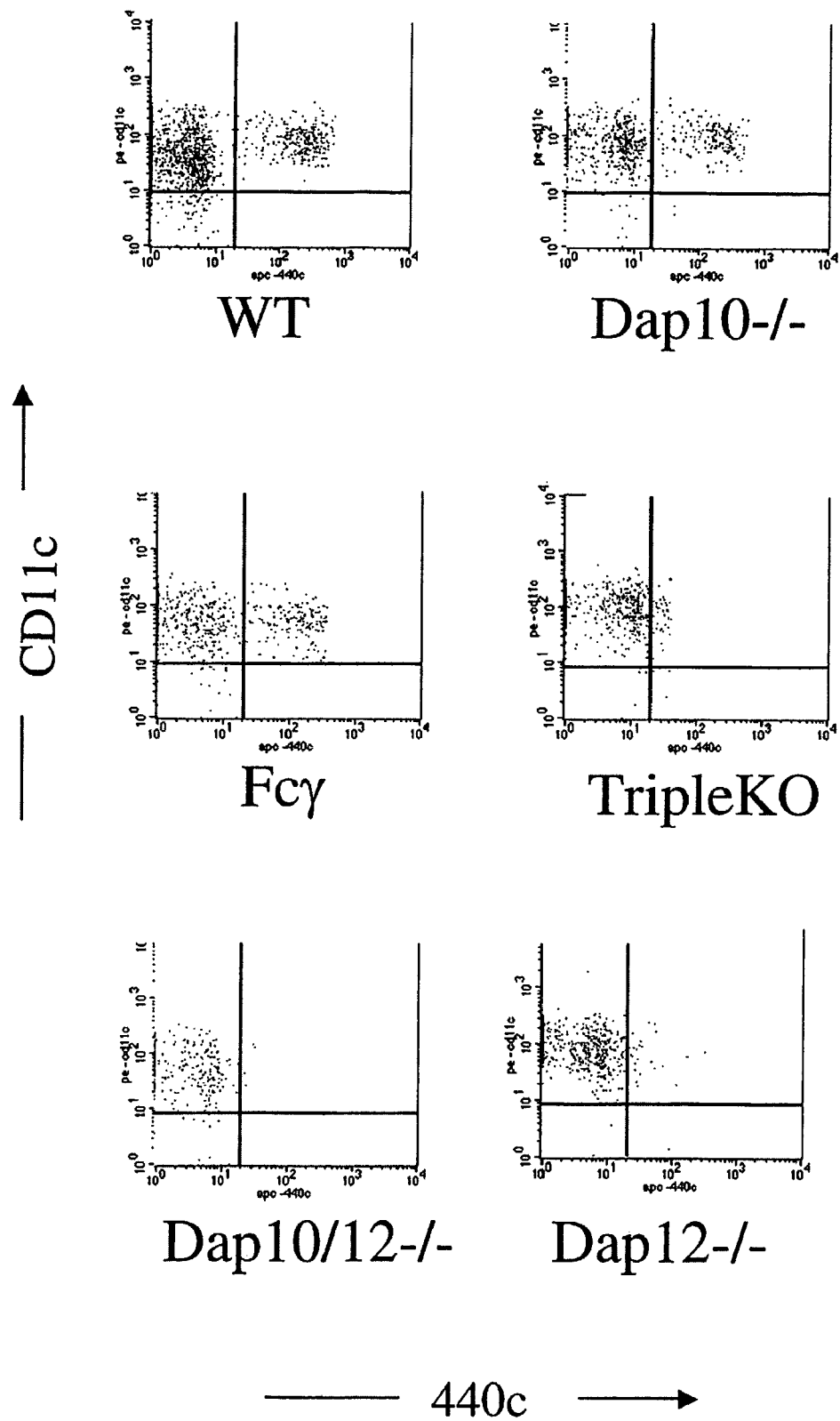
FIGS. 9 and 10 show that 440c is not expressed on the cell surface of IPC in DAP12 deficient living mice.

FIG. 9 shows murine CD11c+ splenocytes from mice deficient in various signaling chains stained with mAb 440C. The specificity of our 440c mAb was demonstrated here in that 440C did not stain in any strain that was DAP 12 deficient.

Figure 10:
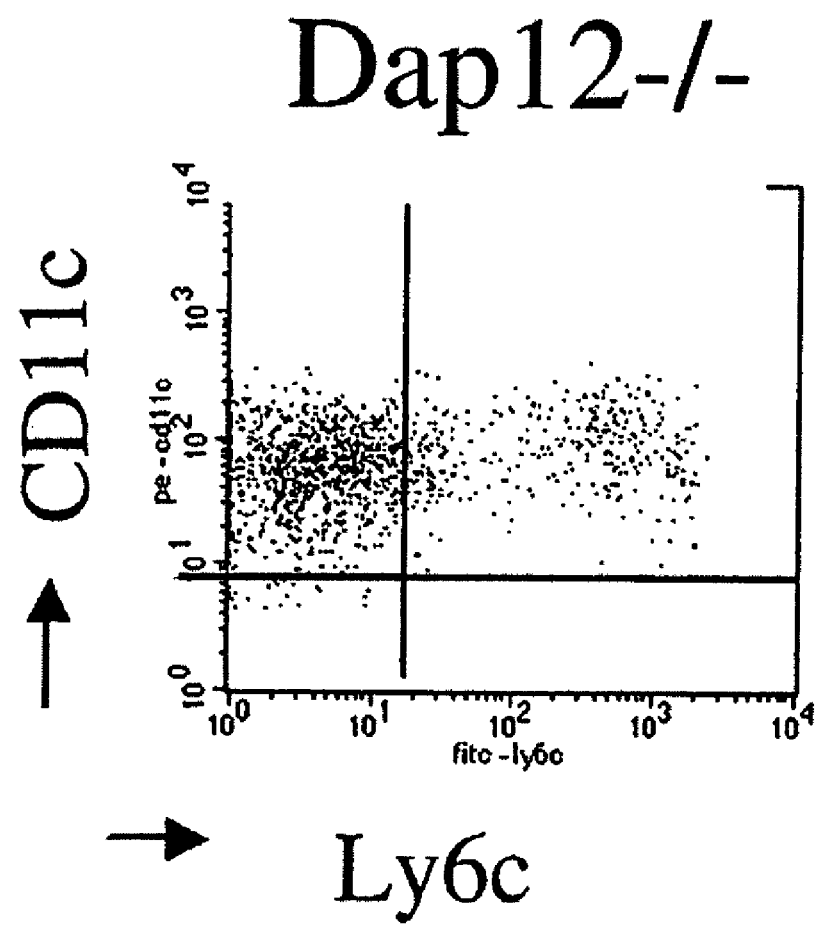

FIG. 10 shows that CD11c+Ly6c+ IPC are present in DAP12 deficient living mice.

DETAILED DESCRIPTION OF THE INVENTION

Unless otherwise defined, technical and scientific terms used herein have the same meaning as commonly understood by one of ordinary skill in the art. Methods and materials similar or equivalent to those described herein can be used in the practice or testing of the present discovery.

All publications, patent applications, patents, and other references mentioned herein are incorporated by reference in their entirety. In addition, examples are illustrative only and not intended to be limiting in any way.

As used herein, the term "interferon" includes any number of proteins which form a closely related group of nonviral proteins of $M_r$ of about 15000 to about 30000 and in humans, the type I IFN family comprises fifteen isotypes expressed upon transcriptional induction (13 IFNs-α, 1 IFN-β, 1 IFN-ω).

As noted herein, the 440c monoclonal antibody of this discovery is conveniently denoted as "440c" by the inventors and in an aspect, is prepared from hybridoma cells obtained by fusing immortal myeloma cells with lymphocyte cells followed by cloning and intentional selection of hybrids that ultimately provides the desired specificity to the murine IPC cell secreting Type I Interferon. Further the term 440c mAB is intended to include throughout the claims and description the 440c mAB and its family of antibodies which have the same or substantially the same specificity as 440c mAb. The family of antibodies have the same antigen specificity, they bind a common DAP12 associated antigen specifically expressed by IPC, including antibodies that bind different epitopes of this antigen.

As used herein, the term "murine" includes living mice, rats, hamsters, rodents and other living members of Muridae, a family of small rodents including mice and rats and all mammals of or relating to the mouse genus Mus. As used herein, the term "murine" includes native, wild and transgenic species. However, 440c mAb recognizes only mouse IPC. In an aspect, the murine is a mouse.

As used herein, the term "serum" includes representative liquid extruded or separated out after blood has clotted and the clot has retracted.

As used herein, the term "treating" refers to the successful administration and presentation of 440c mAb or a composition that includes 440c mAb at time prior to the onset of at least one symptom of an inflammatory response, i.e., prophylactic therapy.

As used herein, "treating" also refers to the administration of 440c mAb or a composition that includes a 440c mAb during or after the onset of at least one symptom of an inflammatory response to alleviate at least one undesired symptom of an inflammatory response.

As used herein, the term "lupus" includes any condition or appearance such as symptomatology which is similar to the symptomatology of lupus in a living clinically detectable lupus afflicted human.

As used herein, the term "natural interferon producing cells" includes one or more of natural interferon producing cell (IPC), plasmacytoid dendritic cell and plasmacytoid monocyte cell and plasmacytoid T cells.

As used herein, the term "animal model" includes a living biosystem such as a living rat, mouse, rodent and hamster as well as a living in vitro cellular system having sufficient and capable biological system functionality to provide clinical detectable indicia of response to a dose of 440c mAb thereto. In an aspect, such an animal model is capable of generating a decipherable biologically recognizable immunological response to an intruder such as virus or a microbe (i.e., it is biologically responsive).

As used herein, the term "expression profile" refers to the clinically detectable biological response of an animal model to the intrusion of a drug (intruder). In an aspect such response is measured (and optionally captured) as a detectable increase or decrease in Type I interferons concentration of serum of the model.

As used herein, the term "antibody" includes both an intact or entire antibody, and a useful antibody fragment or epitope.

As used herein, the term "IPC" includes natural alpha interferon (IFN-α) producing cells which are recognized as plasmacytoid dendritic (DC) precursors in human blood.

As used herein, the term "antibody fragment" includes any useful portion of an antibody, including an epitope, which binds the same antigen that is recognized and capably bound by an intact or nonfragmented antibody. Antibody fragment also includes any synthetic or genetically engineered polypeptide that binds to a specific antigen.

As used herein, the term "animal" is intended to denote a living animal species (preferably mammalian) such as *Homo Sapiens, murine* and *rodentia*. The term "animal" also denotes a population of such a species.

As used herein, the term "inflammation" includes acute and chronic inflammation. Inflammation is characterized by one or more of redness, heat, pain, swelling and loss of function. Inflammation also involves local vasodilatation, extravasation of plasma into the intercellular spaces and at time accumulation of white blood cells and other cells in the injured part of the animal.

As used herein, the term "excessive inflammation" means inflammation more than occurring in normal or a control as for example that of a healthy murine.

As used herein, the term "adjuvant" means a substance or a composition of matter which is capable of enhancing the immune response but which is not in itself capable of mounting a specific immune response against an immunogen.

As used herein, the term "medically effective time" means an amount of elapsed time following presentation of a drug to a biological system for a biological response to have occurred in the system.

As used herein, the expression "effecting presentation to the immune system" is intended to denote that the animal's immune system is subjected to an immunogenic challenge in a controlled manner such as by administration of a drug or antibody thereto.

As used herein, the term "immunogenically effective amount" means an amount of an immunogen which is capable of inducing an immune response, preferably a detectable response.

As used herein, the term "in vivo down-regulation of IPC activity" means a reduction in the living organism of the number of interactions of IPC with other cells and reduction of IPC secreted molecules.

As used herein, the term "carrier" is a substance which is not reactive with the biological system but serving as a means to facilitate administration of a mAb.

As used herein, the term "modulate" means to effect change, adjust or regulate in a biological system.

This discovery provides a novel family of antibodies which are useful against an inflammatory response produced by an inflammatory response inducing agent in a living murine. Typical inflammatory inducing agents include viruses such as MCMV, and (HSV-1) herpes simplex virus 1 and microbes such as *staphylococci aureus*, including prokaryotic microbes and eukaryotic microbes. Additionally, inflammatory states can spontaneously develop in non-manipulated mice or be induced by genetic predisposition.

More in particular, the inventors' novel 440c mAb exclusively detects mouse IPC in lymphoid organs under both normal (non-inflammatory) and inflammatory conditions. Using this antibody, we demonstrate that IPC are normally present in the T cell zone of lymph nodes in the periarteriolar sheets of the spleen (T cell zone) and at the border between the T cell zone and the B cell zone of the spleen (mouse).

The inventors demonstrated that inoculation of peripheral tissues with inflammatory stimuli triggers recruitment of IPC into sentinel lymph nodes, whether the stimuli are able to directly stimulate IPC through TLR or not. Remarkably, the inventors have shown that incubation of IPC with the antibody in vitro or administration of our antibody in vivo dramatically reduce secretion of IFN-α in response to CpG DNA without causing IPC depletion. Thus, our family of antibodies including 440c mAb identify an IPC-specific surface molecule that, when engaged, inhibit IFN-A secretion.

The inventors discovered and prepared a novel mAb denoted as "440c" that exclusively recognizes (specifically) and modulates mouse IPC in lymphoid organs under both normal and sufficiently inflammatory conditions. Using this novel antibody, the inventors demonstrated recruitment of murine IPC into lymph nodes draining inflammations caused by inoculation of either bacterial products or virus in peripheral tissues. Most importantly, the inventors have shown that either incubation of IPC with the antibody in vitro or administration of the antibody in vivo dramatically reduce secretion of IFN-α in response to CpG DNA without causing IPC depletion. Thus, the antibody denoted as "440c" identifies our discovery of our novel, isolated and characterized IPC-specific cell surface molecule that regulates secretion of IFN-α.

In an aspect the invention comprises a method to lower the interferon-alpha serum content of a murine by administering a pharmacological amount of an antibody having the specificity of 440c mAb and including 440c mAb our 440c mAb to the murine by a pharmacologically effective administration means whereby the Type 1 interferon serum content of the murine is lowered.

Examples are provided herein by way of illustration only and are not to be construed as limiting the discovery since various changes and modifications within the spirit of the discovery will become apparent to those skilled in the art from this description.

EXAMPLES

The inventors prepared bone marrow-derived IPC and myeloid DC by culturing harvested bone marrow cells of 129/SvJ mice (Jackson) with FLT3-L and GM-CSF, following a technique previously described[19]. CD11c+ cells were isolated from harvested spleen of ~8-12 week old 129/SvJ mice by digestion with collagenase followed by magnetic sorting[19].

The inventors' novel 440c monoclonal antibody was prepared as follows: Wistar/CRL rats were immunized subcutaneously (s.c) in hind footpads with $10^7$ purified bone-marrow-derived IPC (as an immunogen) and CpG oligodeoxynucleotide (ODN) 1826 (100 μg) as an adjuvant (B cell response) at day 0, 4 and 7. At day 8, popliteal lymph nodes (lymphocytes) of the rats were fused with immortal SP2/0 myeloma cells. (A mutant myeloma cell line lacking erythrocyte hypoxanthine phosphoribosyl transferred (HG3RT) was used to allow hybrids to be selected with ease.) Unfused myeloma cells were killed by growing hybridoma in a composition of hypoxanthine, aminopterin and thymine (HAT) The inventors selected hybridoma supernatants (comprising hybridoma cells) that stained bone marrow-derived IPC and fractions of primary CD11c+ harvested spleen cells, but not bone marrow-derived myeloid DC. In a double selection process, the cells were cloned and screened again and selected for hybridoma supernatants that only stained CD11c+/Ly-6C+/CD11b− splenocytes. The IPC-specific mAb 440c prepared here is a rat IgG2b.

Spleen, thymus, lymph node and liver cell suspensions were prepared by mechanical disruption of tissues and digestion with collagenase. Liver was perfused with phosphate buffered saline (PBS) prior to disruption. Liver cells were further purified on a 30% Percoll gradient. Blood, bone marrow and spleen cells were analyzed after red blood cell lysis. Cells were stained with 44oc (rat IgG2b) and one or two of the following antibodies: anti-B220 (rat IgG2a, FITC or biotin, RA3-6B2), -CD19 (rat IgG2a, FITC, ID3), -CD3ε (hamster IgG, FITC, 145-2C11), -CD11b (rat IgG2a, biotin, 3A33), pan NK cell (rat IgM, APC, DX5), CD8a (rat IgG2a, FITC, 53-6.7), -CD11c (Hamster IgG, PE or Biotin, HL3), and -Ly-6C (rat IgG2c, PE, HK1.4 and rat IgM, FITC, AL-21). Primary antibodies were detected with mouse anti-rat IgG2b (FITC or Biotin) and streptavidin-APC. FcR block (mouse anti-mouse CD16/32, Ly17.1, 17.2, Caltag, 1849 Bayshore Blvd., Burlingame, Calif. 94010, USA) was used to prevent nonspecific binding of antibodies to Fc receptors. All antibodies in this paragraph (other than our 440c mAb) were purchased from BD Biosciences, 2350 Qume Drive, San Jose, Calif. 95131-1807 and Southern Biotechnology Associates (SBA), 160 Oxmoor Blvd., Birmingham, Ala. 35209, USA.

In some tests, stainings were performed on splenocytes derived from mice that had been injected intraperitoneally with MCMV ($10^4$/MOI/mouse) or subcutaneously with CpG ODN 2216 (100 μg/mouse). Stainings were also performed on splenocytes activated in vitro with CpG ODN 1826 and 2216 (3 μg/ml) or HSV-1 (1MOI/cell). For detection of 440c by immunohistochemistry, fresh-frozen sections of lymph nodes and spleens were blocked with normal rabbit serum (1:20, DAKO) and sequentially treated with mAb 440c, biotinylated goat anti-rat IgG (Vector Laboratories), streptavidin-FITC (SBA), immunoperoxidase (HRP)-conjugated anti-FITC (DAKO) aminoethylcarbazole (AEC). Sections were counterstained with Meyer's hematoxylin. In serial histologic sections, anti-CD3 (rat IgG2a, CT-CD3, Caltag Laboratories, Burlingame, Calif.), anti-B220 (rat IgG2a, RA3-6B2, Caltag Laboratories) and anti-IgD (rat IgG2a, Caltag Laboratories) were detected using goat anti-rat IgG (Vector), streptavidin-HRP (Stravigen MultiLink Detection System, Biogenex Laboratories, 4600 Norris Canyon Road, San Ramm, Calif. 94583, USA) and AEC. Negative controls were stained with an irrelevant rat mAb (rat anti-HHV8 ORF73, Advanced Biotechnologies, Rivers Park II, 9108 Guilford Road, Columbia, Md., 21046, USA).

CD11c+ cells were purified from spleens and stained with either mAb 440c or a combination of antibodies specific for CD11c (biotin, HL3), Gr-1 (anti-Gr-1 encompasses Ly-6C and Ly-6G, PE, RB6-8C6) and CD11b (FITC, MI/70). 440c+, 440c−, CD11c+/Gr-1+/CD11b− and CD11c+/Gr-1−/CD11b+/− cells were sorted on a MoFlow cell sorter (Cytomation, 6392 Via Real, Carpinteria, Calif. 93013, USA). Sorted cells ($10^6$/ml, 100,000/well) were stimulated in vitro for 24 hrs with CpG ODN 2216 (3 μg/ml) or murine cytomegalovirus (MCMV, 1 MOI). IFN-α released into culture supernatants was quantitated by Enzyme-Linked Immunosorbent Assay (ELISA) (PBL Biomedical Laboratories) PBL Biomedical Laboratories, 131 Ethel Road West, Suite 6, Piscataway, N.J. 08854-5900, USA.

There are several immunoassays which may be used in analyzing serum for Type I interferons content of the present discovery. Any of the well known immunoassays may be adapted to detect the level of Type I interferons, such as e.g., enzyme linked immunoadsorbent assay (ELISA), fluorescent immunosorbent assay (FIA), chemical linked immunosorbent assay (CLIA), radioimmuno assay (RIA), immunoblotting and Bioassay. For a review of the different immunoassays which may be used, see: The Immunoassay Handbook, David Wild, ed., Stockton Pres New York, 1994. Preferably, a competitive immunoassay with solid phase separation or an immunometric assay for antibody testing is used. See, The Immunoassay Handbook, Chapter 2, supra.

Mice were intentionally effectively inoculated in the left hind footpads and legs with Mycobacterium tuberculosis (Mtb) suspended in RPMI (~500-700 μg/mouse) or HSV-1 KOS strain ($5\times10^5$ plaque forming units/mouse). Bilateral popliteal and inguinal nodes were excised, digested with collagenase and analyzed by flow cytometry.

(a) In vitro blockade: IPC were sorted from spleen and cultured for 24 hrs in medium alone or with varying concentrations of CpG ODN 2216. Cells were cultured on 96 well plates coated with mAb 440c, or a control antibody (IgG2b rat (Sigma Aldrich, 3050 Spruce Street, St. Louis, Mo., 63103 USA)). One day later, culture supernatants were collected and tested for IFN-α by ELISA.

(b) In vivo blockade: Mice were injected subcutaneously with 100 μg of CpG ODN or phosphate buffered saline (PBS) and intraperitoneally (i. p.) with 200 μg of mAb 440c or control IgG2b (Sigma). One day later, serum was collected and IFN-α levels were determined by ELISA.

(c) The inventors have discovered and determined that their 440c mAb does not deplete PC. 129/SvJ mice were treated with two i. p. injections each of 200 μg of mAb 440c at a 24 hrs interval. Splenocytes were isolated 24 hrs after the last injection, stained with anti-CD11c, -Gr-1 and -CD11b mAbs and subjected to flow cytometric analysis.

To establish a murine IPC-specific mAb, the inventors immunized rats with IPC grown from bone marrow precursors and screened for mAbs that stained cultured IPC and subsets of CD11c+ spleen cells. Antibodies recognizing bone marrow-derived myeloid DC were excluded. The mAb 440c stained subsets of CD11c$^+$ and Ly-6C$^+$ splenocytes, whereas it did not recognize myeloid DC, T, B or NK cells (FIG. 1A). Within CD11c$^+$ cells purified from spleen, mAb 440c recognized Ly-6C$^+$/B220$^+$/CD8a$^{+/-}$ cells, but not CD11b$^+$ myeloid DC (FIG. 1B). mAb 440c also exclusively detected CD11c$^+$/Ly-6C$^+$ cells within splenocytes isolated from mice injected in vivo with MCMV (FIG. 1C), CpG ODN 2216, or activated in vitro with CpG ODN or HSV-1. Thus, our mAb 440c selectively identifies cells with the phenotype of mouse IPC.

To provide functional factual evidence that 440c$^+$ cells correspond to IPC, the inventors sorted 440c$^+$ and 440c$^-$ cells from CD11c$^+$ splenocytes, stimulated them in vitro with CpG ODN and MCMV and measured IFN-α secretion. Sorting the cell populations was carried out by labeling the antibody with fluorochromes. (In an aspect, the cell sorter is an automated instrument wherein liquid is forced out a small nozzle and the liquid acts as a carrier or shroud.) (In this aspect, cells are labeled by conjugating them with fluorochromes.) Cells are individually injected into the liquid and the cell sorter is able to sort cells based on the characteristics of light scattered off the cells as a result of impact to the cells by a laser beam.

In control tests, the inventors determined IFN-α responses of IPC and conventional DC that had been sorted using the classical markers (CD11c$^+$/Gr-1$^+$/CD11b$^-$ and CD11c$^+$/Gr-1$^-$/CD11b$^{+/-}$, respectively). As shown in FIG. 2, 440c$^+$ cells secreted markedly higher levels of IFN-α than did 440c$^-$ cells. Importantly, IFN-α responses of 440c$^+$ cells were comparable to those of CD11c+/Gr-1$^+$/CD11b$^-$ IPC. Altogether, these results demonstrate that our mAb 440c selectively recognizes murine IPC.

To investigate the tissue distribution of IPC, the inventors analyzed expression of their 440c mAb, CD11c and Ly-6C in cell suspensions obtained from primary and secondary lymphoid organs. mAb 440 detected IPC in lymph nodes, spleen, thymus, bone marrow and blood (FIG. 3). In general, 440c$^+$ cells co-expressed CD11c and Ly-6C (FIG. 3A). Only 440c$^+$ cells isolated from bone marrow and blood included an additional CD11c$^+$/Ly-6C$^{low}$ population. These cells were B220$^+$ and NK1.1$^-$. Because expression of Ly-6C is induced by IFN-α[27,28], 440c$^+$/CD11c$^+$/Ly-6C$^{low}$ cells may be IPC precursors that have not yet fully acquired the capacity to produce IFN-α. To localize IPC within normal lymphoid organs, the inventors performed immunohistochemistry using the 440c mAb. In the spleen, IPC appeared as single scattered cells or aggregates in the periarteriolar lymphoid sheets (PALS) and at the border of PALS with mantle zone B cells (FIG. 4). In lymph nodes, very few IPC were detectable in the T cell zone of the paracortical area (FIG. 5). IPC numbers varied considerably among the mouse strains analyzed. IPC were readily detectable in 129/SvJ mice, whereas C57Bl/6 and B10.BR mice had consistently lower numbers of IPC. IPC at the border between the T cell zone and mantle zone B cells suggests that IPC may provide help to B cells or modulate T cell help to B cells. Human IPC are located in the T-cell region of lymph nodes in the vicinity of high endothelial venules (HEV) and in the splenic PALS[21,22]. Thus, the tissue distribution of IPC is equivalent in mice or substantially the same and humans.

To determine whether IPC are recruited into inflamed lymph nodes, the inventors compared two animal models of inflammation as described hereafter.

In the inventors' animal model, mice were intentionally humanely inoculated twice with high doses of heat-killed mycobacteria tuberculosis (Mtb), which induced strong inflammation by engaging TLR2 on macrophages[29,30]. Mtb does not directly stimulate IPC, as these cells do not express of TLR2[6-9]. In another animal model, mice were intentionally infected once with live HSV-1, which stimulates IPC through TLR9[11] and induces a modest influx of IPC into lymph nodes after footpad injection[25]. Inoculations were performed in the left mouse footpad to generate ipsilateral popliteal and inguinal lymphadenitis. After 48-72 hours, bilateral popliteal and inguinal nodes were excised for flow cytometric analysis. In the Mtb model we observed a significantly higher proportion of IPC in reactive lymph nodes in comparison to those from contralateral nodes (FIG. 5). IPC infiltration was less pronounced in the HSV-1 model. The inventors also observed a significant variability depending on the mouse strain.

In 129/SvJ mice, the inventors consistently observed a 5-10 fold increase in the relative percent of IPC in inflamed lymph nodes (FIG. 5); less dramatic increases were detected in other strains. However, since the total cell number in lymph nodes expanded 2-4 fold during inflammation, even a small increase in the percent of IPC reflects a considerable increase in the total number of IPC.

Our results demonstrated that inflammation is the stimulus that drives the recruitment of IPC into sentinel lymph nodes, whether the pathogenic stimuli are able to directly stimulate IPC through TLR (i.e. HSV-1) or not (i.e. heat-inactivated mycobacterium tuberculosis). IPC recruitment varies depending on the strength of inflammatory stimulus and the mouse strain.

To determine whether the cell surface molecule recognized by our mAb 440c is directly involved in IPC function, IPC were sorted from a harvested mouse spleen using conventional markers CD11c and Gr-1, and cultured in vitro with CpG ODN on plates coated with either our mAb 440c, a control antibody (IgG2b rat (Sigma Aldrich)) and no antibody. Measurement of IFN-α responses showed that our mAb 440c significantly reduced secretion of IFN-α induced by CpG ODN (FIG. 6A). To corroborate this result in vivo, we simultaneously injected CpG ODN s.c. and either mAb 440c, a control antibody, and PBS i. p. and measured serum levels of IFN-α. As shown in FIG. 6B, administration of a single dose of our mAb 440c almost completely abolished the IFN-α response to CpG ODN in vivo. Notably, administration of mAb 440c did not cause depletion of IPC (FIG. 6C). We concluded that blockade of IFN-A response by our mAb 440c is due to the engagement of a cell surface molecule selectively expressed on IPC that inhibits IFN-α response to CpG ODN.

The inventors have successfully identified and characterized, isolated and prepared and obtained a family of novel mAbs (denoted as "440c") that selectively recognize mouse IPC. Advantageously, our 440c mAb is specific for IPC not only under physiological conditions, but also after activation of immune cells in vitro and in vivo with microbial components or viruses. Thus, our 440c mAb provides a unique useful research tool to precisely identify and localize IPC in murine tissues in both normal (healthy state) and inflammatory and infections (disease state) conditions.

Using our antibody, the inventors demonstrated the presence of IPC in blood and in primary and secondary lymphoid organs, corroborating previous studies performed using a combination of different mAbs[13]. Importantly, we found that IPC are located in the T cell zone of the lymph nodes and in the PALS of the spleen, paralleling the localization previously described for human IPC. The presence of IPC in the T cell areas of secondary lymphoid organs strongly supports a role of IPC in regulating adaptive T cell responses. In general, 440c$^+$ IPC have the CD11c$^+$/Ly-6C$^+$/B220$^+$/CD11b$^-$ phenotype originally described for IPC. The inventors detected a 440$^+$ cell population in bone marrow and blood that expresses low levels of Ly-6C. As expression of Ly-6C is induced by IFN-A[27,28], these cells may represent IPC precursors that have not yet fully developed their IFN-α production potential.

Pathologists know IPC as cells with plasma cell-like morphology or "plasmacytoid monocytes"[21,22]. These cells are particularly abundant around HEVs in lymph nodes of patients with certain chronic lymphadenitis[22]. This notion, together with the expression of L-selectin and receptors for proinflammatory chemokines, has suggested that IPC may be recruited from blood to lymph nodes during inflammatory conditions. In this study, we provided experimental evidence for this hypothesis. Using our mAb 440c, we detected a significant increase of IPC in murine lymph nodes draining a local infection as compared to control lymph nodes. High doses of Mtb were more effective than HSV-1 in promoting IPC recruitment, although Mtb is unable to directly stimulate IPC through TLRs. Thus, massive IPC accumulation like that observed in several human lymphadenites most likely requires strong and/or prolonged inflammatory stimuli, whether they are able to directly stimulate IPC through TLRs or not. Intriguingly, the number of IPC detected under both normal and inflammatory conditions greatly varied depending on the mouse strain. 129/SvJ mice harbor relatively high numbers of IPC that are clearly recruited to draining lymph nodes following inflammation. In other strains, fairly small numbers of IPC were detected and recruitment was less evident following inflammation. Thus, IPC differentiation and migration may be influenced by genetic factors. Recently, it was shown that certain tumors release chemokines that attract IPC and that tumor-associated IPC induce tolerogenic T cell responses[34]. Our mAb 440c provides an important practical functional research tool having functional utility to investigate IPC recruitment and function in mouse tumor models.

A remarkable utilitarian property of our 440c mAb is its ability to block secretion of IFN-α in response to CpG ODN in vitro and in vivo without depleting IPC. Thus, our 440c mAb identifies a novel cell surface molecule that, upon engagement, negatively regulates the secretion of type I IFN by IPC.

It has been proposed that excessive secretion of type I IFN by IPC in response to microbes may contribute to the pathogenesis of autoimmune responses[36-38]. Consistent with this, patients with systemic lupus erithematosus (SLE) have infiltrating IPC in skin lesions[39] and high levels of IFN-α in their serum[40]. In addition, treatment of virally infected patients with IFN-α may trigger SLE-like syndromes and, in particular, the appearance of autoantibodies. Our mAb 440c allows testing this hypothesis by modulating IFN-α responses of IPC in animal models of intentionally induced infections and autoimmune diseases.

Recently it was shown that certain tumors release chemokines that attract IPC and that tumor-associated IPC induce tolerogenic T cell responses$_{37}$. In an aspect, mAb 440c provides an important tool to investigate IPC recruitment and function in murine tumor models.

Antibodies were made using the protocol as described in paragraphs 00020 and 00088. Alternatively, antibodies with the same specificity could be generated by immunizing animals directly with the purified antigen. These other antibodies are not clonal with 440c, meaning their sequences differ and although they bind the same antigen, they may bind different epitopes on that antigen.

In an aspect, our discovery is employed in a diagnostic method. In another aspect, our discovery is employed in a therapeutic method.

Advantageously, such beneficial and biologically distinctive properties of our 440c mAb allows our novel expression profiling of diseased and nondiseased animal models leading to predictive capably as to efficacy of pharmaceutical drug candidates in symptomatic and clinical treatment of autoimmune disease. The capability of expression profiling provides a means for comparing the efficacy of various drug candidates against a disease state having inflammatory conditions such as lupus. mAb 440c can be used to target pharmaceutical candidates specifically to IPC.

In an aspect, such expression profiles are capably employed to evaluate the biosystem of the animal model to interaction with an exogenous chemical or intentional intruder presenting itself to an animal model.

In an aspect, an illustrative investigation protocol is employed as (a) induce a disease state in a murine by viral or microbial infection or by genetic predisposition (b) induce a different disease state in a different mouse (c) administering 440c mAb to a murine, optimally with and without a drug. In each instance, such as the above, an expression profile is generated. An expression profile may be employed to diagnose the extent or severity of the disease and/or to compare the effect of the administration of 440c mAb to the infected murine and/or compare effects of various drugs. In an aspect, such protocols are therapeutic and/or diagnostic.

In an aspect the conjugated drug/pharmaceutical candidate is a toxin, such as saporin, creating an immunotoxin.

Although mAb 440c does not deplete IPC, such depletion may be achieved by conjugating 440c with toxins, such as saporin[42] to create an immunotoxin. We tested this possibility on IPC cultured in vitro from bone marrow cells with FLT3-L. Cultured $CD11c^+$ $B220^{hi}$ IPC, which correspond to fully developed IPC, expressed high levels of 440c (see FIGS. 7A and B). A minor subset of CD11c+ B220⁻ cells displayed low levels of 440c antigen and may correspond to a developmental intermediate of IPC. Upon treatment of bone marrow derived IPC with biotinylated 440c mAb followed by an avidin-saporin conjugate, ~70% of $CD11c^+$ $B220^{hi}$ $440c^{bright}$ IPC were depleted from culture within 36 hours (FIGS. 7C and D). Analysis of IPC depletion at later time points was not reliable as IPC poorly survived in vitro in the absence of stromal cells and, therefore, IPC numbers were reduced not only in 440c treated cultures but also in control cultures. Nevertheless, these results indicate that mAb 440c conjugated with a toxin represent a useful tool to achieve IPC depletion.

Intentional depletion of IPC by 440c-based immunotoxin was performed as follows. Non-adherent cells were harvested from bone marrow cultures treated with FLT3-Ligand and characterized for expression of 440c, CD11c and B220 by flow cytometry. Cells were incubated in vitro with biotinylated 440c or biotinylated control antibody (rat Ig G, BD Biosciences) for about 15 minutes on ice, washed and incubated with avidinylated saporin (Advanced Targeting Systems, San Diego, Calif.) for 15 minutes on ice. Cells were washed and cultured in media containing FLT3-L for 36 hours. Cells were then harvested and analyzed by flow cytometry.

In an aspect, our novel murine (animal) model herein operates on the basis of an intentional infection of a sample of a living healthy murine to create a disease state murine model. Advantageously, this diseased state animal model provides an optimal reliable useful (research tool) means to identify pharmaceutical drugs efficacious against lupus like symptomatology.

Successful screening of pharmaceutical drugs having possible therapeutic efficacy against one or more diseases is highly desired. In that regard, in a further embodiment, a method is provided for successfully screening one or a multiplicity of candidate pharmaceuticals, which comprises contacting our murine animal model existing in an autoimmune disease state with an effective amount of a pharmaceutical chemical such as in a pharmaceutical composition and measuring response to that treated chemical in terms of modulation of Type I interferons level in the serum of the diseased murine. In an aspect, a database of efficacy of the test candidate drugs is established whereby the extent to which a chemical treats at least one symptom of an inflammatory response in an animal is determined. Such treatment encompasses administering one or more doses of a prospective drug to an animal model and recording the biological effect such as reduction in the amount of Type I interferons in the serum or modulation of interferon-α. If desired a dosage rate titration is carried out.

In a further embodiment, a useful method is provided for effectively managing a data library of one or more pharmaceuticals or pharmaceutical chemicals which comprises obtaining an Type I interferons expression profile of a response of IPC to the contact of an agent with the animal model comprising IPC, storing that profile in a database, storing at least one additional expression profile of another pharmaceutical in the database, setting up a means for comparing more than one expression profile with another expression profile, comparing the expression profile of a first pharmaceutical with a profile of a second pharmaceutical based on a pre-established or ordered standard/hierarchy of comparison and ranking the pharmaceuticals in an order of activity with respect to effect on the animal model. In an aspect, an Type I interferons profile comprises the Type I interferons content of a serum sample from a living animal model or animal. This utility provides a system for hierarchical ranking or prioritization of chemicals based on their expression profiling in an animal model based on this discovery.

In an aspect, the results of screening are employed to identify and advance one or more candidate pharmaceuticals or drugs to an advanced stage of further stage of testing or evaluation, including possibly commercialization. In another aspect, the results of screening are employed to terminate or alter further testing or screening on a pharmaceutical or drug candidate. In another aspect, the method and apparatus herein are used to evaluate and validate the target or locus of activity for or of the drug or pharmaceutical candidate.

Advantageously, an animal model system can be configured as having chronic autoimmune disease by the intentional creation of viral infection of a sample, such as try a pathogen incubation wherein the pathogen is a virus or microbe. This opportunistically creates a disease state animal model readily useful for expression profiling of IPC secretion of Type 1 interferons.

In an aspect, the animal model comprises a living mouse or living mice cells.

In an aspect, this discovery is employed in determining the role of IPC in a disease in which Type I interferons cause one or more diseases.

In an aspect, the antibody of this discovery is pharmacologically employed with a suitable pharmaceutical carrier. If desired, a pharmaceutical pack or kit comprises one or more containers filled with one or more pharmaceutical compositions of this discovery.

In an aspect, 440c is used as a biomarker to monitor the levels of IPC in a murine patient. In an aspect, 440c is conjugated to a dye or marker and administered to the patient. The amount of 440c that remains within the patient is monitored as a readout for level of IPC present in the patient. His level can be indicative of disease progress or heightened/lowered immune response.

Advantageously, this discovery possesses specific and practical utility as an improved method of predictive medicine wherein a biological system approach is employed to identify and provide drugs, etc. to treat chronic murine autoimmune diseases based upon an understanding of the relevant disease state of an individual. This discovery also has utility as a method of clinical preventive medicine by identifying and providing by therapeutic methods to circumvent an existing disease state. Together such advance allows the enhanced practice of personalized medicine.

The formations may be presented in unit dosage form and prepared by pharmacy methods. Typically, methods of preparing a pharmaceutical composition include admixing the 440c mAb with a carrier which comprises one or more optional ingredients. In an aspect, formulations are prepared by uniformly, intimately admixing the 440c mAb into a composition with a compatible liquid carrier or a finely divided solid carrier.

In an aspect, the 440c mAb is admixed directly into the food of a murine's diet, as an additive, or supplement.

In an aspect, formulations suitable for parenteral administration comprise sterile aqueous preparation of the composition, or dispersions of sterile powders that include the composition, which are isotonic with the blood of the recipient useful. Isotonic agents include sugars, buffers, and sodium chloride. The compositions can be prepared in water or mixed with a nontoxic surfactant. Dispersions can be prepared using water, ethanol, a polyol (such as glycerol, propylene glycol, liquid polyethylene glycols, and the like), vegetable oils and glycerol esters. In an aspect, the dosage form is stable, sterile and fluid.

In an aspect, useful formulations include one or more optional ingredients including diluents, buffers, binders, disintegrants, surface active agents, thickeners, lubricants, and preservatives (including antioxidants).

In an aspect, those which can be admitted by formulation include subcutaneous, intramuscular, intraperitoneal, intravenous, and aerosol administration.

DAP12, Genbank accession number AF024637 also known as KARAP or pp16, was first identified as a 12-16 kDa protein that coimmunoprecipitates with activating receptors in both mouse and man. DAP12 is essential for surface expression of some associated receptors, and even in overexpressing transfectants, associated receptors are only expressed at very low levels in the absence of DAP12. A positively charged residue in the transmembrane domain of activation receptors interacts with the negatively charged aspartic acid in the transmembrane domain of DAP12. Under normal circumstances, the charged residues in the transmembrane domains would cause them to be retained in the ER and eventually degraded in the proteosome. Association of the two molecules masks the charged residues, allowing translocation to the cell surface. Thus, mice genetically deficient in DAP12 lack surface expression of DAP12 associated molecules.

The cytoplasmic domain of DAP12 contains an immunoreceptor tyrosine-based activation motif (ITAM) that becomes tyrosine phosphorylated upon receptor engagement. Once both of the tyrosine residues are phosphorylated, the ITAM binds protein tyrosine kinase Syk or Zap70. A cascade of protein tyrosine phosphorylation follows, including phosphorylation of phospholipase Cγ1, and Cb1, and mitogen activated protein kinases, resulting in calcium mobilization and cellular activation. Cross-linking of activation receptors associated with DAP12 may result in upregulation of adhesion molecules and costimulatory molecules and cytokine and chemokine secretion.

The inventors have determined that mAb 440C does not bind to IPC in animals deficient in DAP12 (FIGS. 9 and 10). This effect is not due to an absence of IPC in DAP12 deficient animals because normal numbers of CD11c+Ly6C+B220+ cells are found. Mice deficient in other signaling chains, such as Fcγ or DAP10 continue to stain with mAb 440C. Therefore, inventors discovered that the antigen recognized by mAb 440C is associated with the DAP12 signaling chain, requiring the presence of DAP12 for cell surface expression.

REFERENCES

1. Perussia B, Fanning V, Trinchieri G. A leukocyte subset bearing HLA-DR antigens is responsible for in vitro alpha interferon production in response to viruses. Nat Immun Cell Growth Regul. 1985; 4:120-137
2. Fitzgerald-Bocarsly P. Human natural interferon-alpha producing cells. Pharmacol Ther. 1993; 60:39-62.
3. Cederblad B, Alm G V. Infrequent but efficient interferon-alpha-producing human mononuclear leukocytes induced by herpes simplex virus in vitro studied by immuno-plaque and limiting dilution assays. J Interferon Res. 1990; 10:65-73
4. Siegal F P, Kadowaki N, Shodell M, Fitzgerald-Bocarsly P A, Shah K, Ho S, Antonenko S, Liu Y J. The nature of the principal type 1 interferon-producing cells in human blood. Science. 1999; 284:1835-1837.
5. Cella M, Jarrossay D, Facchetti F, Alebardi O, Nakajima H, Lanzavecchia A, Colonna M. Plasmacytoid monocytes migrate to inflamed lymph nodes and produce large amounts of type I interferon. Nat Med. 1999; 5:919-923.
6. Bauer M, Redecke V, Ellwart J W, Scherer B, Kremer J P, Wagner H, Lipford G B. Bacterial CpG-DNA triggers activation and maturation of human CD11c−, CD123+ dendritic cells. J Immunol. 2001; 166:5000-5007.
7. Jarrossay D, Napolitani G, Colonna M, Sallusto F, Lanzavecchia A. Specialization and complementarity in microbial molecule recognition by human myeloid and plasmacytoid dendritic cells. Eur J Immunol. 2001; 31:3388-3393.
8. Kadowaki N, Ho S, Antonenko S, Malefyt R W, Kastelein R A, Bazan F, Liu Y J. Subsets of human dendritic cell precursors express different toll-like receptors and respond to different microbial antigens. J Exp Med. 2001; 194:863-869.
9. Krug A, Towarowski A, Britsch S, Rothenfusser S, Hornung V, Bals R, Giese T, Engelmann H, Endres S, Krieg A M, Hartmann G. Toll-like receptor expression reveals CpG DNA as a unique microbial stimulus for plasmacytoid dendritic cells which synergizes with CD40 ligand to induce high amounts of IL-12. Eur J Immunol. 2001; 31:3026-3037.
10. Krieg A M. CpG motifs in bacterial DNA and their immune effects. Annu Rev Immunol. 2002; 20:709-760
11. Lund J, Sato A, Akira S, Medzhitov R, Iwasaki A. Toll-like receptor 9-mediated recognition of Herpes simplex virus-2 by plasmacytoid dendritic cells. J Exp Med. 2003; 198:513-520
12. Cella M, Facchetti F, Lanzavecchia A, Colonna M. Plasmacytoid dendritic cells activated by influenza virus and CD40L drive a potent TH1 polarization. Nat Immunol. 2000; 1:305-310.
13. Asselin-Paturel C, Boonstra A, Dalod M, Durand I, Yessaad N, Dezutter-Dambuyant C, Vicari A, O'Garra A, Biron C, Briere F, Trinchieri G. Mouse type I IFN-producing cells are immature APCs with plasmacytoid morphology. Nat Immunol. 2001; 2:1144-1150.
14. Brasel K, De Smedt T, Smith J L, Maliszewski C R. Generation of murine dendritic cells from flt3-ligand-supplemented bone marrow cultures. Blood. 2000; 96:3029-3039
15. Krug A, Uppaluri R, Facchetti F, Dorner B G, Sheehan K C, Schreiber R D, Cella M, Colonna M. IFN-producing cells respond to CXCR3 ligands in the presence of CXCL12 and secrete inflammatory chemokines upon activation. J Immunol. 2002; 169:6079-6083
16. Penna G, Vulcano M, Sozzani S, Adorini L. Differential migration behavior and chemokine production by myeloid and plasmacytoid dendritic cells. Hum Immunol. 2002; 63:1164-1171
17. Fonteneau J F, Gilliet M, Larsson M, Dasilva I, Munz C, Liu Y J, Bhardwaj N. Activation of influenza virus-specific CD4+ and CD8+ T cells: a new role for plasmacytoid dendritic cells in adaptive immunity. Blood. 2003; 101:3520-3526
18. Dalod M, Salazar-Mather T P, Malmgaard L, Lewis C, Asselin-Paturel C, Briere F, Trinchieri G, Biron C A. Interferon alpha/beta and interleukin 12 responses to viral infections: pathways regulating dendritic cell cytokine expression in vivo. J Exp Med. 2002; 195:517-528.
19. Krug A, Veeraswamy R, Pekosz A, Kanagawa O, Unanue E R, Colonna M, Cella M. Interferon-producing cells fail to induce proliferation of naive T cells but can promote expansion and T helper 1 differentiation of antigen-experienced unpolarized T cells. J Exp Med. 2003; 197:899-906
20. Boonstra A, Asselin-Paturel C, Gilliet M, Crain C, Trinchieri G, Liu Y J, O'Garra A. Flexibility of mouse classical and plasmacytoid-derived dendritic cells in directing T helper type 1 and 2 cell development: dependency on antigen dose and differential toll-like receptor ligation. J Exp Med. 2003; 197:101-109
21. Vollenweider R, Lennert K. Plasmacytoid T-cell clusters in non-specific lymphadenitis. Virchows Arch B Cell Pathol Incl Mol Pathol. 1983; 44:1-14
22. Facchetti F, De Wolf-Peters C, Marocolo D, De Vos R. Plasmacytoid monocytes in granulomatous lymphadenitis and in histiocytic necrotizing lymphadenitis. Sarcoidosis. 1991; 8:170-171.
23. Nakano H, Yanagita M, Gunn M D. CD11c(+)B220(+)Gr-1(+) cells in mouse lymph nodes and spleen display characteristics of plasmacytoid dendritic cells. J Exp Med. 2001; 194:1171-1178.
24. Vanbervliet B, Bendriss-Vermare N, Massacrier C, Homey B, De Bouteiller O, Briere F, Trinchieri G, Caux C. The Inducible CXCR3 Ligands Control Plasmacytoid Dendritic Cell Responsiveness to the Constitutive Chemokine Stromal Cell-derived Factor 1 (SDF-1)/CXCL12. J Exp Med. 2003; 198:823-830
25. Smith C M, Belz G T, Wilson N S, Villadangos J A, Shortman K, Carbone F R, Heath W R. Cutting edge: conventional CD8 alpha+ dendritic cells are preferentially involved in CTL priming after footpad infection with herpes simplex virus-1. J Immunol. 2003; 170:4437-4440
26. Bjorck P. Isolation and characterization of plasmacytoid dendritic cells from Flt3 ligand and granulocyte-macrophage colony-stimulating factor-treated mice. Blood. 2001; 98:3520-3526.
27. Dumont F J, Coker L Z. Interferon-alpha/beta enhances the expression of Ly-6 antigens on T cells in vivo and in vitro. Eur J Immunol. 1986; 16:735-740

28. Schlueter A J, Krieg A M, de Vries P, Li X. Type I interferon is the primary regulator of inducible Ly-6C expression on T cells. J Interferon Cytokine Res. 2001; 21:621-629
29. Heldwein K A, Fenton M J. The role of Toll-like receptors in immunity against mycobacterial infection. Microbes Infect. 2002; 4:937-944
30. Brightbill H D, Libraty D H, Krutzik S R, Yang R B, Belisle J T, Bleharski J R, Maitland M, Norgard M V, Plevy S E, Smale S T, Brennan P J, Bloom B R, Godowski P J, Modlin R L. Host defense mechanisms triggered by microbial lipoproteins through toll-like receptors. Science. 1999; 285:732-736
32. Barchet W, Cella M, Odermatt B, Asselin-Paturel C, Colonna M, Kalinke U. Virus-induced interferon alpha production by a dendritic cell subset in the absence of feedback signaling in vivo. J Exp Med. 2002; 195:507-516
33. Eloranta M L, Alm G V. Splenic marginal metallophilic macrophages and marginal zone macrophages are the major interferon-alpha/beta producers in mice upon intravenous challenge with herpes simplex virus. Scand J Immunol. 1999; 49:391-394
34. Zou W, Machelon V, Coulomb-L'Hermin A, Borvak J, Nome F, Isaeva T, Wei S, Krzysiek R, Durand-Gasselin I, Gordon A, Pustilnik T, Curiel D T, Galanaud P, Capron F, Emilie D, Curiel T J. Stromal-derived factor-1 in human tumors recruits and alters the function of plasmacytoid precursor dendritic cells. Nat Med. 2001; 7:1339-1346.
35. Dzionek A, Sohma Y, Nagafune J, Cella M, Colonna M, Facchetti F, Gunther G, Johnston I, Lanzavecchia A, Nagasaka T, Okada T, Vermi W, Winkels G, Yamamoto T, Zysk M, Yamaguchi Y, Schmitz J. BDCA-2, a novel plasmacytoid dendritic cell-specific type II C-type lectin, mediates antigen capture and is a potent inhibitor of interferon alpha/beta induction. J Exp Med. 2001; 194:1823-1834.
36. Ronnblom L, Alm G V. An etiopathogenic role for the type I IFN system in SLE. Trends Immunol. 2001; 22:427-431.
37. Vallin H, Perers A, Alm G V, Ronnblom L. Anti-double-stranded DNA antibodies and immunostimulatory plasmid DNA in combination mimic the endogenous IFN-alpha inducer in systemic lupus erythematosus. J Immunol. 1999; 163:6306-6313.
38. Jego G, Palucka A K, Blanck J P, Chalouni C, Pascual V, Banchereau J. Plasmacytoid dendritic cells induce plasma cell differentiation through type I interferon and interleukin 6. Immunity. 2003; 19:225-234
39. Farkas L, Beiske K, Lund-Johansen F, Brandtzaeg P, Jahnsen F L. Plasmacytoid dendritic cells (natural interferon-alpha/beta-producing cells) accumulate in cutaneous lupus erythematosus lesions. Am J Pathol. 2001; 159: 237-243.
40. Bennett L, Palucka A K, Arce E, Cantrell V, Borvak J, Banchereau J, Pascual V. Interferon and granulopoiesis signatures in systemic lupus erythematosus blood. J Exp Med. 2003; 197:711-723.
41. Natural Alpha Interferon-Producing Cells Respond to Human Immunodeficiency Virus Type 1 with Alpha Interferon Production and Maturation in Dendritic Cells, Akihito Yonezawa, et al., Journal of Virology, 2003 Mah; 77(6): 377-3784.
42. Flavell D J. Saporin immunotoxins. Curr Top Microbiol Immunol. 1998; 234:57-61

While our discovery has been described in terms of various specific embodiments, those skilled in the art will recognize that the discovery can be practiced with modification.

What is claimed is:

1. An isolated monoclonal antibody that specifically binds to a cell surface molecule of a murine interferon producing cell, wherein the monoclonal antibody is mAb 440c.

2. The monoclonal antibody in accordance with claim 1 wherein the cell surface molecule regulates secretion of interferon-α such that the monoclonal antibody significantly reduces secretion of interferon-α without causing interferon producing cell depletion.

3. The monoclonal antibody of claim 1 wherein the monoclonal antibody is a rat IgG2b.

4. The monoclonal antibody of claim 1, wherein the monoclonal antibody is prepared by immunizing Wistar/CRL rats subcutaneously with purified mouse bone marrow interferon producing cells, fusing popliteal lymph nodes of the rats with immortal SP2/0 myeloma, selecting hybridoma supernatants that successfully stain bone marrow derived interferon producing cells and subsets of $CD11C^+$ spleen cells, further selecting hybridoma supernatants that stained $CD11C^+/Ly-6^+/CD11b^-$ splenocytes and recovering such supernatants containing the monoclonal antibody.

* * * * *